(12) United States Patent
Kraft et al.

(10) Patent No.: US 12,264,361 B2
(45) Date of Patent: Apr. 1, 2025

(54) IMAGE SENSOR STRUCTURES AND RELATED METHODS

(71) Applicants: Illumina, Inc., San Diego, CA (US); Illumina Cambridge Limited, Great Abington (GB)

(72) Inventors: Lewis Kraft, Acworth, GA (US); Craig Lee Hetherington, Foster City, CA (US); Craig M. Ciesla, Mountain View, CA (US); Michael Burek, San Diego, CA (US); Jeffrey Fisher, San Diego, CA (US); Jason Betley, Buntingford (GB)

(73) Assignees: Illumina, Inc., San Diego, CA (US); Illumina Cambridge Limited, Great Abington (GB)

( * ) Notice: Subject to any disclaimer, the term of this patent is extended or adjusted under 35 U.S.C. 154(b) by 777 days.

(21) Appl. No.: 17/643,454

(22) Filed: Dec. 9, 2021

(65) Prior Publication Data

US 2022/0186307 A1 Jun. 16, 2022

Related U.S. Application Data

(60) Provisional application No. 63/123,741, filed on Dec. 10, 2020.

(51) Int. Cl.
*C12Q 1/6869* (2018.01)
*H01L 27/146* (2006.01)

(52) U.S. Cl.
CPC ...... *C12Q 1/6869* (2013.01); *H01L 27/14625* (2013.01)

(58) Field of Classification Search
CPC ......... H01L 27/14625; H01L 27/14634; H01L 27/1461; C12Q 1/6869; C12Q 2537/143;
(Continued)

(56) References Cited

U.S. PATENT DOCUMENTS

2011/0127619 A1* 6/2011 Chen .................. G01N 21/6454
257/E29.166
2011/0172129 A1 7/2011 Lee et al.
(Continued)

FOREIGN PATENT DOCUMENTS

WO 2020005503 A1 1/2020

OTHER PUBLICATIONS

International Search Report and Written Opinion, PCT/US2021/062549, mailing date Apr. 13, 2022.

*Primary Examiner* — Sang H Nguyen
(74) *Attorney, Agent, or Firm* — Stephen P. Scuderi; HESLIN ROTHENBERG FARLEY & MESITI P.C.

(57) ABSTRACT

An image sensor structure includes an image layer having an array of light detectors disposed therein. A device stack is disposed over the image layer. An array of light guides is disposed in the device stack. Each light guide is associated with a light detector. An array of nanowells is disposed over the device stack. Each nanowell is associated with a first light guide of the array of light guides. A first primer set is disposed throughout a first well region of each nanowell. A second primer set is disposed throughout a second well region of each nanowell. The second well region is adjacent the first well region. The first and second primer sets are operable to attach a forward strand cluster of forward polynucleotide strands in the first well region and a reverse strand cluster of reverse polynucleotide strands in the second well region.

20 Claims, 20 Drawing Sheets

(58) Field of Classification Search
CPC ........ C12Q 2565/619; C12Q 2563/159; C12Q 2535/122; G01N 21/6454
See application file for complete search history.

(56) References Cited

U.S. PATENT DOCUMENTS

2019/0088463 A1* 3/2019 Li ..................... G01N 21/6454
2019/0196108 A1    6/2019 Cai
2019/0198553 A1* 6/2019 Cai .................... G01N 21/6454
2022/0352228 A1* 11/2022 Emadi ............... H01L 27/14625

* cited by examiner

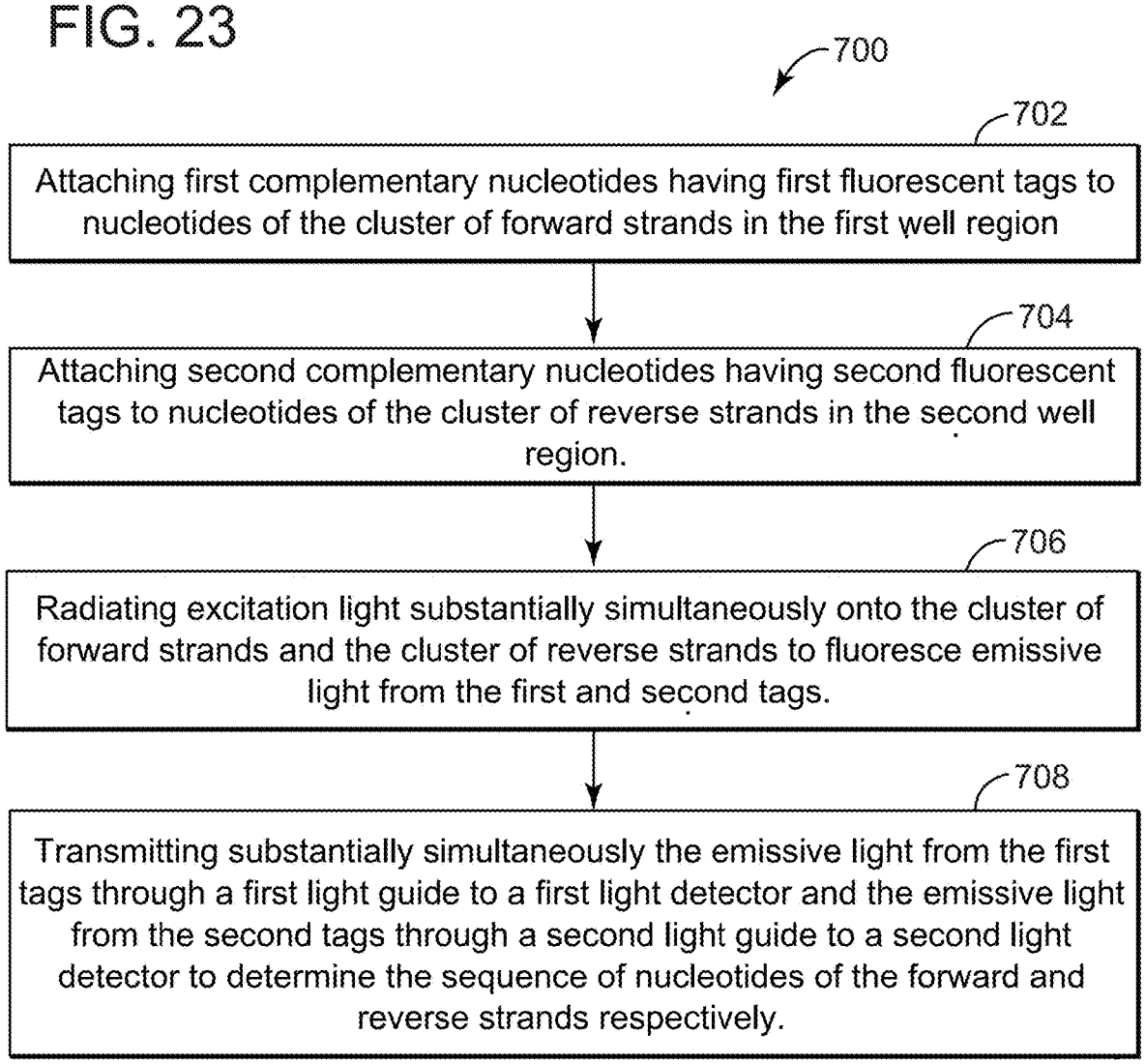

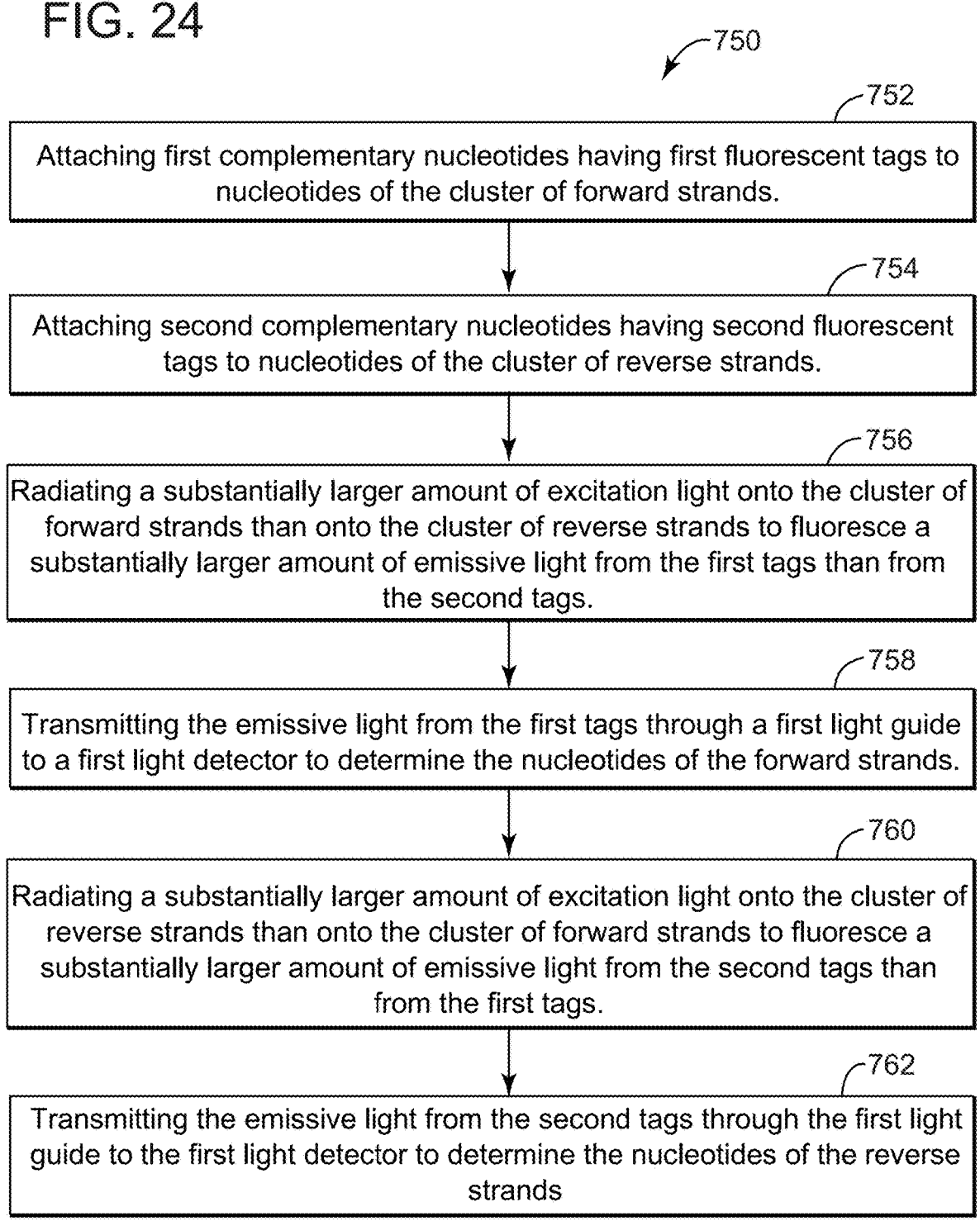

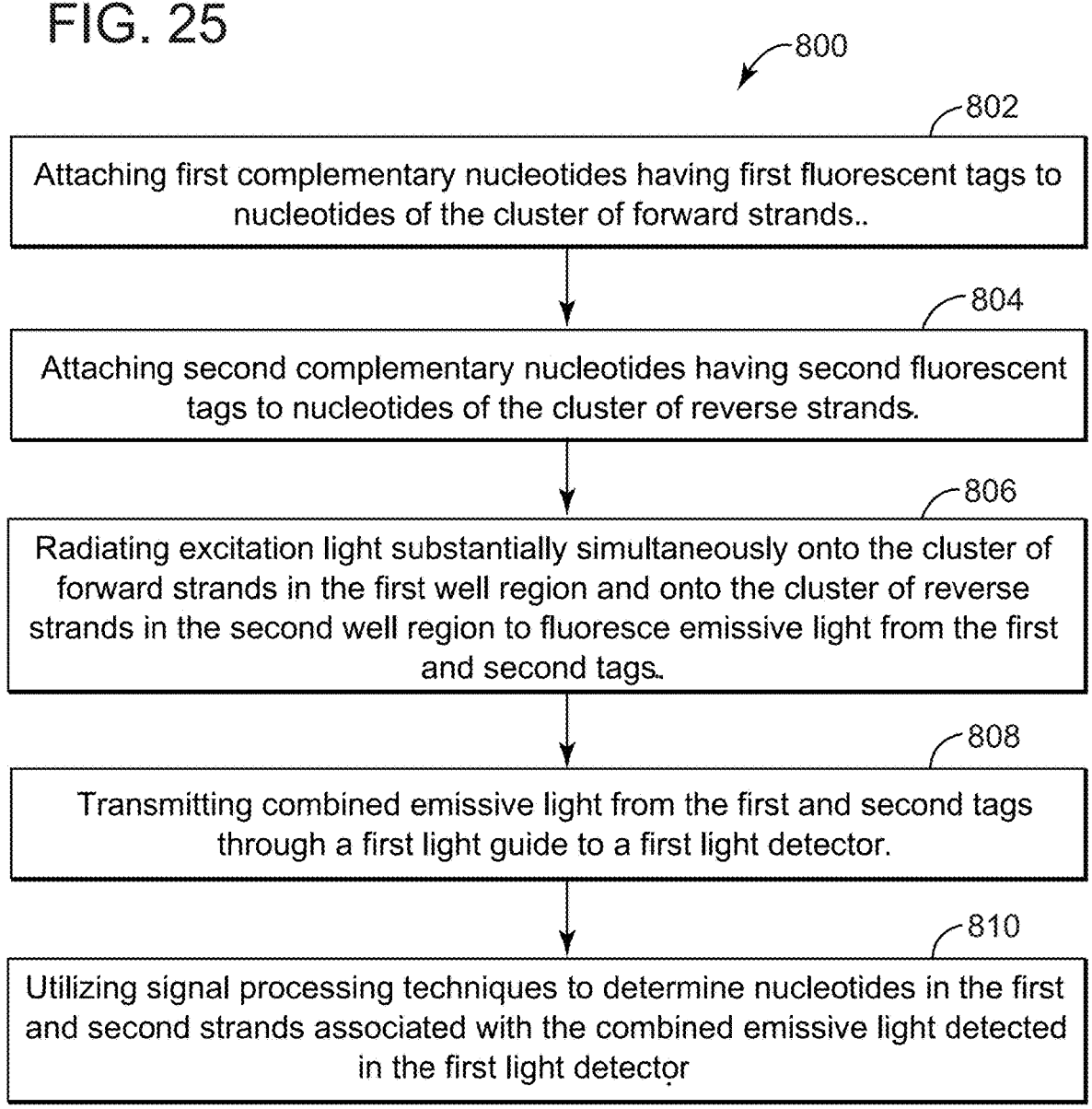

IMAGE SENSOR STRUCTURES AND RELATED METHODS

CROSS-REFERENCE TO RELATED APPLICATIONS

This application is a non-provisional of, and claims the benefit of the filing date of, U.S. provisional application 63/123,741, filed Dec. 10, 2020, entitled, "IMAGE SENSOR STRUCTURES AND RELATED METHODS," the contents of which are incorporated herein by reference.

BACKGROUND

Image sensor structures may be coupled with such microfluidic devices as flow cells to form a sensor system. The sensor system may be, for example, a biosensor system. Such sensor systems often utilize high density arrays of nanowells disposed in a top layer of a passivation stack of one or more layers (herein the "passivation stack") of the image sensor structure to perform controlled reaction protocols on polynucleotide strands disposed within the nanowells. The reaction protocols may, for example, determine the order of nucleotides within the strands.

In an example of such a reaction protocol, polynucleotide strands (such as clusters of DNA fragments, nucleic-acid molecular chains, or the like) that are disposed in a nanowell array of an image sensor structure may be tagged with an identifiable label (such as a fluorescently labeled nucleotide base) that is delivered to the strands via fluid flow through a flow cell. One or more excitation lights may then be directed onto the labeled strands within the nanowells. The labeled strands may then emit photons of an emissive light, indicative of the order of nucleotide bases in the strand, which may be transmitted through the passivation stack and into light guides of the image sensor structure that are associated (e.g., located directly below) with each nanowell.

The light guides direct the emissive light photons to light detectors disposed within the image sensor structure and associated with the light guides. The light detectors detect the emissive light photons. Device circuitry within the image sensor structure then processes and transmits data signals using those detected photons. The data signals may then be analyzed to reveal the sequence of nucleotide bases within the strands. An example of such a sequencing process is known as sequencing by synthesis.

In an example of preparation of polynucleotide strands for a sequencing process, a first adapter and a different second adapter are often added to the ends of the polynucleotide strands, to form what is known as a DNA library. The adapters are complementary to forward and reverse primers, such as oligonucleotide fragments (oligos), which are anchored in the nanowells of the flow cell by their 5' ends. Thus, the DNA library to be sequenced thus hybridizes (seeds) to the forward and reverse primers and is amplified on the solid support forming a DNA cluster.

The forward and reverse primer contain chemical cleavage sites, such that the forward strands or reverse strands may be cleaved and removed independently. Sequencing of the forward and reverse strands is carried out in a sequential manner, by first removing reverse strands, blocking their 3' ends, and sequencing the forward strands resulting in a read 1, and then after the cluster has been reamplified, the forward strands are removed, their 3' ends blocked, and sequencing the reverse strands, resulting in a read 2.

Problematically however, because synthesis of forward strands and reverse strands are done serially, the process is very time consuming. Additionally, the larger the nanowells (for example for larger clusters or multiple clusters), the more the probability that polyclonality (i.e., more than one type of strand being initially seeded in the nanowell and then simultaneously amplified into a polyclonal cluster) may occur. Moreover, the closer clusters are to each other, the more the probability of crosstalk (i.e., light emitted from one cluster entering the light guide of another cluster and registering on an unassociated light detector) may occur.

Accordingly, there is a need for an image sensor structure that enables a faster sequencing process than that of serially synthesizing first the forward strand and then the reverse strand of a polynucleotide strand. Moreover, there is a need to reduce the probability of polyclonality if such a faster sequencing process may involve larger nanowells. Additionally, there is a need to reduce the probability of crosstalk if such a faster sequencing process may involve multiple clusters in close proximity to each other.

BRIEF DESCRIPTION

The present disclosure offers advantages, benefits, and alternatives over the prior art by providing image sensor structures that enable simultaneous paired end sequencing (or reading) of adjacent forward strand and reverse strand clusters. Simultaneous paired-end sequencing allows users to sequence both forward and reverse complementary strands of a cluster at the same time. Additionally, the image sensors of the present disclosure include various structures that enable a reduced probability of polyclonality and crosstalk for adjacent forward and reverse strand clusters.

An image sensor structure in accordance with one or more aspects of the present disclosure includes an image layer. The image layer includes an array of light detectors disposed therein. A device stack is disposed over the image layer. An array of light guides is disposed in the device stack. Each light guide is associated with a light detector of the array of light detectors. An array of nanowells is disposed over the device stack. Each nanowell of the array of nanowells is associated with a first light guide of the array of light guides. A first primer set is disposed throughout a first well region of each nanowell. A different second primer set is disposed throughout a second well region of each nanowell. The second well region is adjacent the first well region at a region interface. The first and second primer sets are operable to attach a forward strand cluster of forward polynucleotide strands in the first well region and to attach an adjacent reverse strand cluster of reverse polynucleotide strands in the second well region.

In some examples of the image sensor structure, each nanowell of the array of nanowells is associated with a second light guide of the array of light guides. The first well region is disposed over the first light guide. The second well region is disposed over the second light guide.

In some examples of the image sensor structure, an area of the first well region is smaller than an area of the second well region.

In some examples of the image sensor structure, the first and second well regions having substantially equal widths. The first well region has a length that is 90% or less of a length of the second region.

In some examples of the image sensor structure, the first well region includes a first section that is disposed over the entire first light guide. The first section has a first section width. A second section extends from the first section to the region interface. The second section has a second section width that is less than the first section width. The second well region includes a third section that is disposed over the entire second light guide. The third section has a third section width. A fourth section extends from the third section to the region interface. The fourth section has a fourth section width that is less than the third section width. The second section width of the first well region and the fourth section width of the second well region are substantially equal.

In some examples of the image sensor structure, the first section and third sections have substantially circular shapes. The first and third section widths are diameters of the first and third sections respectively.

In some examples of the image sensor structure, the second and fourth section widths are 50% or less than the first and third section widths respectively.

In some examples of the image sensor structure, an opaque layer is disposed between the array of light guides and the first and second well regions of each nanowell. The opaque layer extends under the entire region interface of the first and second well regions. The opaque layer covers less than an entire portion of top surfaces the first and second light guides associated with each nanowell.

In some examples of the image sensor structure, the opaque layer does not cover any portion of the top surfaces of first and second light guides associated with each nanowell.

In some examples of the image sensor structure, the opaque layer covers greater than 10% of the top surfaces of the first and second light guides associated with each nanowell.

In some examples of the image sensor structure, the first light guide is associated with a first light detector of the array of light detectors. The second light guide is associated with a second light detector of the array of light detectors. Each nanowell is associated with the first and second light guides having a width that is less than the pitch between the first and second light detectors. The first and second light guides extend from their associated nanowell to their associated first and second light detectors at an acute angle relative to each other.

In some examples of the image sensor structure, the first well region is disposed over a first portion of the first light guide. The second well region is disposed over a second portion of the first light guide.

In some examples of the image sensor structure, a waveguide layer is disposed between the array of light guides and the first and second well regions of each nanowell. A first waveguide is disposed in the waveguide layer and extends under the first well region. The first waveguide is operable to illuminate excitation light on a forward strand cluster attached in the first well region. A second waveguide is disposed in the waveguide layer and extends under the second well region. The second waveguide is operable to illuminate excitation light on a reverse strand cluster attached in the second well region.

In some examples of the image sensor structure, the first waveguide is operable to illuminate excitation light on a forward strand cluster of forward polynucleotide strands attached in the first well-region. Additionally, the second waveguide is operable to illuminate excitation light on a reverse strand cluster of reverse polynucleotide strands attached in the second well-region.

In some examples of the image sensor structure, a passivation stack is disposed over the device stack, where the array of nanowells is disposed in the passivation stack.

In some examples of the image sensor structure, the first well region of each nanowell is disposed over a first portion of the associated first light guide. The second well region of each nanowell is disposed over a second portion of the associated first light guide. An array of first waveguides is disposed over the device stack. Each first waveguide is associated with a nanowell of the array of nanowells. Each first waveguide is operable to illuminate excitation light on a forward strand cluster of forward polynucleotide strands attached in the first well-region of the first waveguide's associated nanowell. An array of second waveguides is disposed over the device stack. Each second waveguide is associated with a nanowell of the array of nanowells. Each second waveguide is operable to illuminate excitation light on a reverse strand cluster of reverse polynucleotide strands attached in the second well-region of the second waveguide's associated nanowell.

In some examples of the image sensor structure, a waveguide layer is disposed between the array of light guides and the first and second well regions of each nanowell. Each first waveguide of the array of waveguides is disposed in the waveguide layer and extends under the first well region of the first waveguide's associated nanowell. Each second waveguide of the array of waveguides is disposed in the waveguide layer and extends under the second well region of the second waveguides associated nanowell.

In some examples of the image sensor structure, a passivation stack is disposed over the device stack, wherein the array of nanowells is disposed in the passivation stack. Each first waveguide of the array of first waveguides is disposed in the passivation stack adjacent a side of the first waveguide's associated nanowell. Each second waveguide of the array of waveguides is disposed in the passivation stack adjacent an opposing side of the second waveguide's associated nanowell.

In some examples of the image sensor structure, each first waveguide of the array of first waveguides is operable to illuminate excitation light on a cluster of polynucleotide strands attached in the first or second well-region of a nanowell adjacent to the first waveguide's associated nanowell. Each second waveguide of the array of second waveguides is operable to illuminate excitation light on a cluster of polynucleotide strands attached in the first or second well-region of a nanowell adjacent to the second waveguide's associated nanowell.

In some examples of the image sensor structure, the first well region and second well region are bounded by a wall of the well, except at the region interface.

Another image sensor structure in accordance with one or more aspects of the present disclosure includes an image layer comprising an array of light detectors disposed therein. A device stack is disposed over the image layer. An array of light guides is disposed in the device stack. Each light guide is associated with a light detector of the array of light detectors. An array of nanowells is disposed over the device stack. Each nanowell of the array of nanowells is associated with a first and a second light guide of the array of light guides. A first primer set is disposed throughout a first well region of each nanowell. The first well region is disposed over the first light guide. A different second primer set is disposed throughout a second well region of each nanowell. The second well region is disposed over the second light guide and adjacent the first well region at a region interface. The first and second primer sets are operable to attach a forward strand cluster in the first well region and to attach an adjacent reverse strand cluster in the second well region. An area of the first well region is smaller than an area of the second well region.

In some examples of the image sensor structure, the first well region includes a first section having a substantially circular shape that is disposed over the entire first light guide. The first section has a first section diameter. A second section extends from the first section to the region interface. The second section has a second section width that is less than the first section diameter. The second well region includes a third section having a substantially circular shape that is disposed over the entire second light guide. The third section has a third section diameter. A fourth section extends from the third section to the region interface. The fourth section has a fourth section width that is less than the third section diameter. The second section width of the first well region and the fourth section width of the second well region are substantially equal.

In some examples of the image sensor structure, an opaque layer is disposed between the array of light guides and the first and second well regions of each nanowell. The opaque layer extends under the entire region interface of the first and second well regions. The opaque layer covers less than an entire portion of top surfaces the first and second light guides associated with each nanowell.

In some examples of the image sensor structure, the opaque layer does not cover any portion of the top surfaces of first and second light guides associated with each nanowell.

In some examples of the image sensor structure, the first light guide is associated with a first light detector of the array of light detectors. The second light guide is associated with a second light detector of the array of light detectors. Each nanowell is associated with the first and second light guides having a width that is less than the pitch between the first and second light detectors. The first and second light guides extend from their associated nanowell to their associated first and second light detectors at an acute angle relative to each other.

Another image sensor structure in accordance with one or more aspects of the present disclosure includes an image layer comprising an array of light detectors disposed therein. A device stack is disposed over the image layer. An array of light guides is disposed in the device stack. Each light guide is associated with a light detector of the array of light detectors. An array of nanowells is disposed over the device stack. Each nanowell of the array of nanowells is associated with a first light guide of the array of light guides. A first primer set is disposed throughout a first well region of each nanowell. The first well region is disposed over a first portion of the first light guide. A different second primer set is disposed throughout a second well region of each nanowell. The second well region is disposed over a second portion of the first light guide. The second well region is adjacent the first well region at a region interface. The first and second primer sets are operable to attach a forward strand cluster in the first well region and to attach an adjacent reverse strand cluster in the second well region.

In some examples of the image sensor structure, a waveguide layer is disposed between the array of light guides and the first and second well regions of each nanowell. A first waveguide is disposed in the waveguide layer and extends under the first well region. The first waveguide is operable to illuminate excitation light on a forward strand cluster attached in the first well region. A second waveguide is disposed in the waveguide layer and extends under the second well region. The second waveguide is operable to illuminate excitation light on a reverse strand cluster attached in the second well region.

In some examples of the image sensor structure, an array of first waveguides is disposed over the device stack. Each first waveguide is associated with a nanowell of the array of nanowells. Each first waveguide is operable to illuminate excitation light on a forward strand cluster of forward polynucleotide strands attached in the first well-region of the first waveguide's associated nanowell. An array of second waveguides is disposed over the device stack. Each second waveguide is associated with a nanowell of the array of nanowells. Each second waveguide is operable to illuminate excitation light on a reverse strand cluster of reverse polynucleotide strands attached in the second well-region of the second waveguide's associated nanowell.

A method of simultaneous paired end sequencing in accordance with one or more aspects of the present disclosure includes seeding a first primer set in a first well region of a nanowell of an image sensor structure with a polynucleotide strand. A second primer set in a second well region of the nanowell is deactivated to disable seeding of other polynucleotide strands in the second well region. The first polynucleotide strand is amplified into a plurality of forward and reverse strands throughout the first well region. The reverse strands are cleaved from the first well region to form a forward strand cluster in the first well region. The second primer set in the second well region is activated to enable seeding and amplification in the second well region. The forward strand cluster of the first well region is amplified into the second well region to form a plurality of forward and reverse strands in the second well region. The forward strands are cleaved from the second well region to form a reverse strand cluster in the second well region. The forward strand cluster in the first well region and the reverse strand cluster in the second well region are sequenced substantially simultaneously.

In some examples of the method, deactivating the second primer set includes masking the second well region, and activating the second primer set comprises unmasking the second well region.

In some examples of the method, first complementary nucleotides having first fluorescent tags are attached to nucleotides of the forward strand cluster in the first well region. Second complementary nucleotides having second fluorescent tags are attached to nucleotides of the reverse strand cluster in the second well region. Excitation light is radiated substantially simultaneously onto the forward strand cluster and the reverse strand cluster to fluoresce emissive light from the first and second tags. The emissive light from the first tags is transmitted through a first light guide to a first light detector and the emissive light from the second tags is transmitted through a second light guide to a second light detector to determine the sequence of nucleotides of the forward and reverse strands respectively.

In some examples of the method, the first well region has an area that is smaller than an area of the second well-region.

In some examples of the method, the first well region includes a first and a second section. The first section is disposed over the entire first light guide. The first section has a first section width. The second section extends from the first section to a region interface between the first and second well regions. The second section has a second section width that is less than the first section width. The second well region includes a third and a fourth section. The third section is disposed over the entire second light guide. The third section has a third section width. A fourth section extends from the third section to the region interface. The fourth section has a fourth section width that is less than the third section width.

In some examples of the method, an opaque layer is disposed between the first and second light guides and the first and second well regions. The opaque layer extends under an entire region interface of the first and second well regions. The opaque layer covers less than an entire portion of the first and second light guides.

In some examples of the method, the nanowell has a width that is less than a pitch between the first and second light detectors. The first and second light guides extend to their associated first and second light detectors at an acute angle relative to each other.

In some examples of the method, the first well-region is disposed over a first portion of a first light guide. The second well-region is disposed over a second portion of the first light guide.

In some examples of the method, first complementary nucleotides having first fluorescent tags are attached to nucleotides of the forward strand cluster. Second complementary nucleotides having second fluorescent tags are attached to nucleotides of the reverse strand clusters. A substantially larger amount of excitation light is radiated onto the forward strand cluster than onto the reverse strand cluster to fluoresce a substantially larger amount of emissive light from the first tags than from the second tags. The emissive light is transmitted from the first tags through a first light guide to a first light detector to determine the nucleotides of the forward strands. A substantially larger amount of excitation light is radiated onto the reverse strand cluster than onto the forward strand cluster to fluoresce a substantially larger amount of emissive light from the second tags than from the first tags. The emissive light is transmitted from the second tags through the first light guide to the first light detector to determine the nucleotides of the reverse strands.

In some examples of the method, a waveguide layer is disposed between the first light guide and the first and second well regions. A first waveguide is disposed in the waveguide layer, wherein the first waveguide extends under the first well-region, but not under the second well region. A second waveguide is disposed in the waveguide layer, wherein the second waveguide extends under the second well-region, but not under the first well region. The excitation light is radiated through the first waveguide and onto the forward strand cluster. The excitation light is radiated through the second waveguide and onto the reverse strand cluster.

In some examples of the method, a first waveguide is disposed over the first light guide. A second waveguide is disposed over the first light guide. The excitation light is radiated through the first waveguide and onto the forward strand cluster. The excitation light is radiated through the second waveguide and onto the reverse strand cluster.

In some examples of the method, first complementary nucleotides having first fluorescent tags are attached to nucleotides of the forward strand cluster. Second complementary nucleotides having second fluorescent tags are attached to nucleotides of the reverse strand cluster. Excitation light is radiated substantially simultaneously onto the forward strand cluster in the first well region and onto the reverse strand cluster in the second well region to fluoresce emissive light from the first and second tags. Combined emissive light from the first and second tags is transmitted through a first light guide to a first light detector. Signal processing techniques are utilized to determine nucleotides in the forward and reverse strands associated with the combined emissive light detected in the first light detector.

In some examples of the method, sequencing substantially simultaneously includes receiving substantially simultaneously emissive light from first tags of the forward strands to a first light detector and emissive light from second tags of the reverse strands to a second light detector to determine the sequence of nucleotides of the forward and reverse strands respectively.

In some examples of the method, sequencing substantially simultaneously includes receiving emissive light from first tags of the forward strands to a first light detector and emissive light from second tags of the reverse strands to the first light detector to determine the sequence of nucleotides of the forward and reverse strands respectively.

In some examples of the method, emissive light received from first tags of the forward strands to a first light detector is received substantially simultaneously as emissive light received from second tags of the reverse strands to the first light detector.

In some examples of the method, emissive light received from first tags of the forward strands to a first light detector is received before emissive light is received from second tags of the reverse strands to the first light detector.

It should be appreciated that all combinations of the foregoing concepts and additional concepts discussed in greater detail below (provided such concepts are not mutually inconsistent) are contemplated as being part of the subject matter disclosed herein and/or may be combined to achieve the particular benefits of a particular aspect. In particular, all combinations of claimed subject matter appearing at the end of this disclosure are contemplated as being part of the subject matter disclosed herein.

DRAWINGS

The disclosure will be more fully understood from the following detailed description taken in conjunction with the accompanying drawings, in which:

FIG. 23 depicts an example of another flow diagram of a method of simultaneous paired end sequencing, in accordance with aspects described herein;

FIG. 24 depicts an example of another flow diagram of a method of simultaneous paired end sequencing, in accordance with aspects described herein; and FIG. 25 depicts an example of another flow diagram of a method of simultaneous paired end sequencing, in accordance with aspects described herein.

DETAILED DESCRIPTION

Certain examples will now be described to provide an overall understanding of the principles of the structure, function, manufacture, and use of the methods, systems, and devices disclosed herein. One or more examples are illustrated in the accompanying drawings. Those skilled in the art will understand that the methods, systems, and devices specifically described herein and illustrated in the accompanying drawings are non-limiting examples and that the scope of the present disclosure is defined solely by the claims. The features illustrated or described in connection with one example maybe combined with the features of other examples. Such modifications and variations are intended to be included within the scope of the present disclosure.

The terms "significantly", "substantially", "approximately", "about", "relatively," or other such similar terms that may be used throughout this disclosure, including the claims, are used to describe and account for small fluctuations, such as due to variations in processing from a reference or parameter. Such small fluctuations include a zero fluctuation from the reference or parameter as well. For example, they can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

Figure 1:
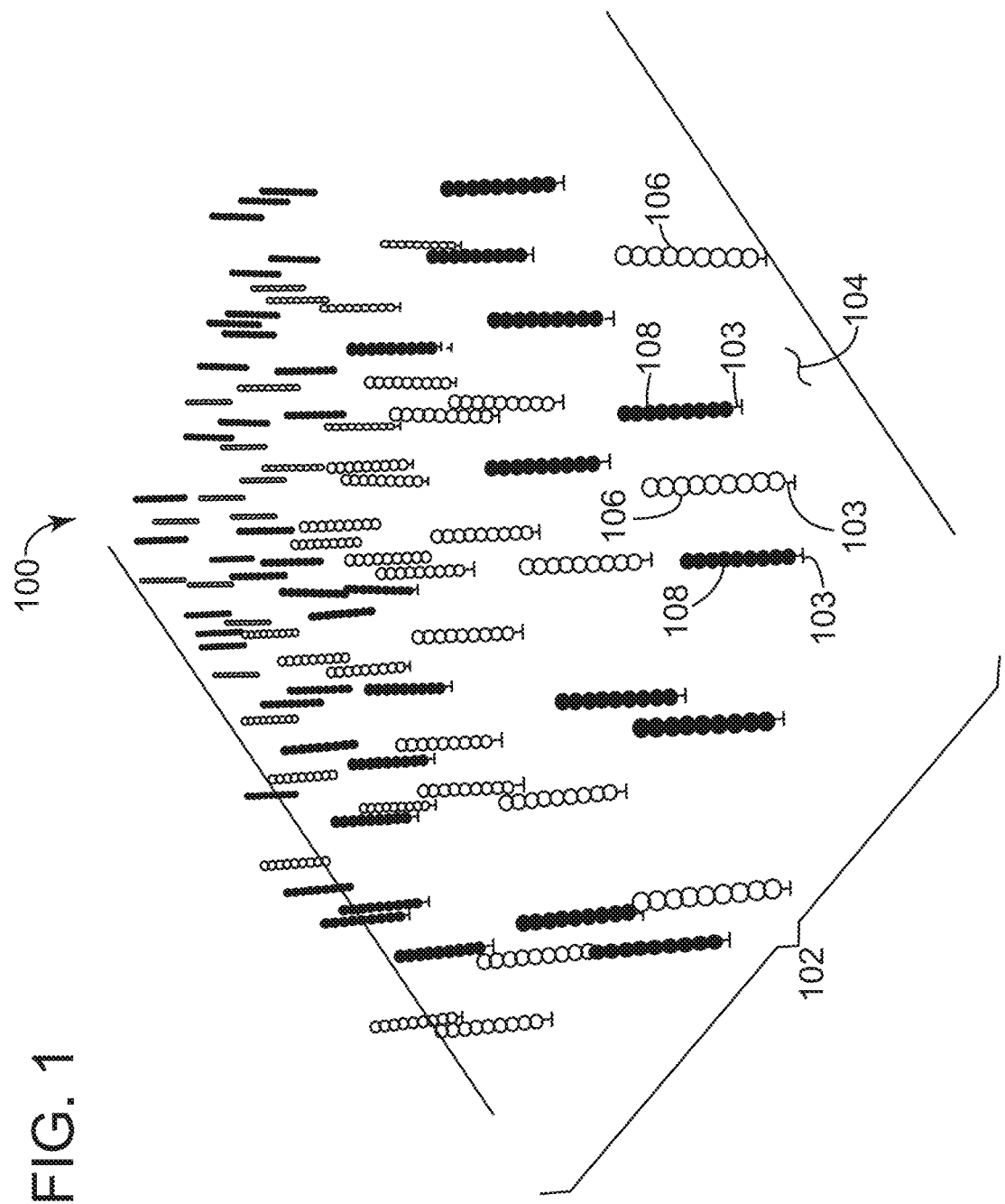
FIG. 1 depicts an example of a set of primer molecules anchored to a well region of an image sensor structure, according to aspects described herein.

Referring to FIG. 1, an example is depicted of a set of primer molecules (i.e., a primer set) 102 anchored (via, for example, a chemical anchor 103) to a well region 104 of an image sensor structure 100, according to aspects described herein. The primer set 102 may, included at least two types of oligonucleotides (i.e., oligos) 106, 108 that activate the well region 104 of the image sensor structure 100 to be able to anchor polynucleotide strands 110 (see FIG. 2) to the image sensor structure 100. Oligos 106 and 108 may be referred to herein as the forward and reverse oligos or primers respectively.

Figure 2:
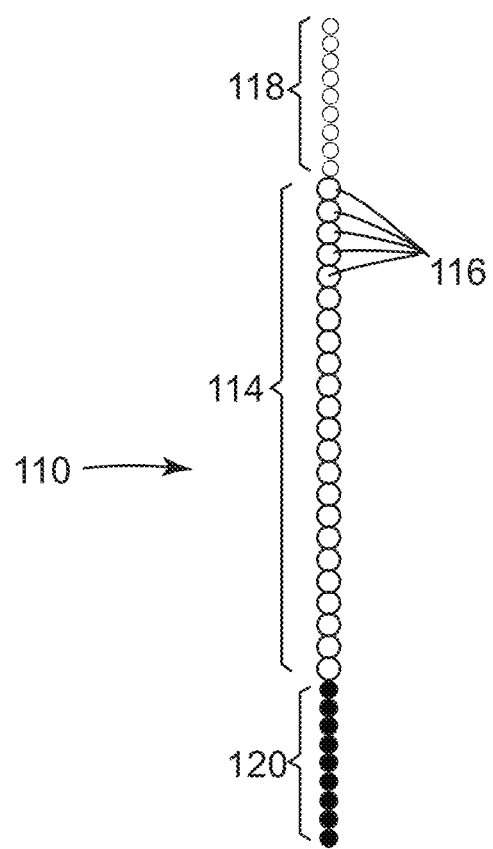
FIG. 2 depicts an example of a polynucleotide strand that may be introduced to a well region of an image sensor structure, according to aspects described herein.
Figure 7:
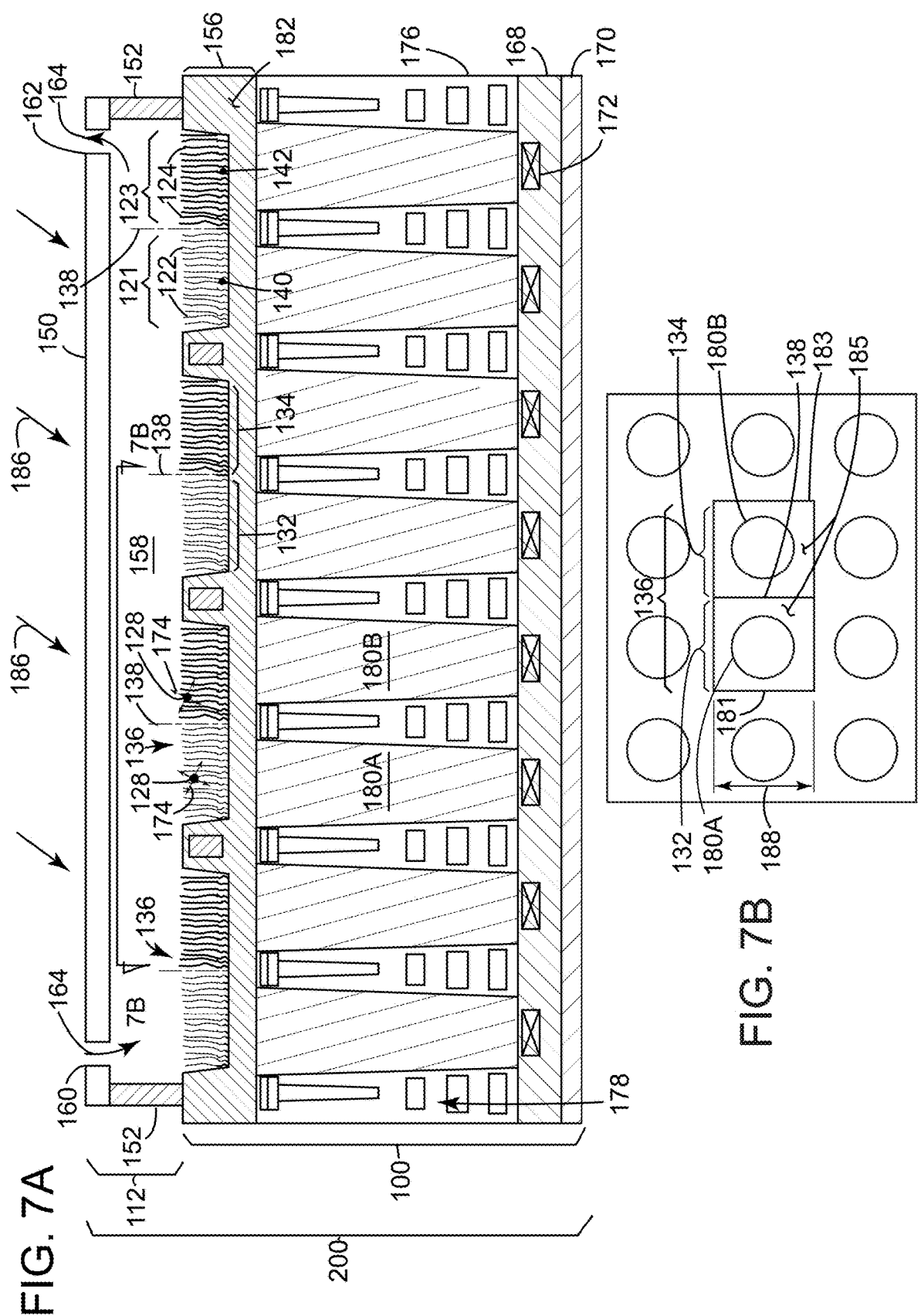
FIG. 7A depicts an example of a cross sectional side view of a sensor system having a flow cell attached to an image sensor structure, according to aspects described herein.
FIG. 7B depicts an example of a top view of the image sensor structure of FIG. 7A taken along the line 7B-7B of FIG. 7A, according to aspects described herein.

Referring to FIG. 2, an example is depicted of a polynucleotide strand 110 that may be introduced to the well region 104 of the image sensor structure 100 via a flow cell 112 (see FIG. 7A), according to aspects described herein. The polynucleotide strand 110 may include a polynucleotide fragment (such as a DNA or RNA fragment) 114 of an unknown sequence of nucleotides 116.

The polynucleotide strand 110 also may include a pair of forward end adapters 118 and reverse end adapters 120. The pair of adapters 118, 120 may be complementary to the oligos 106, 108.

Figure 3:
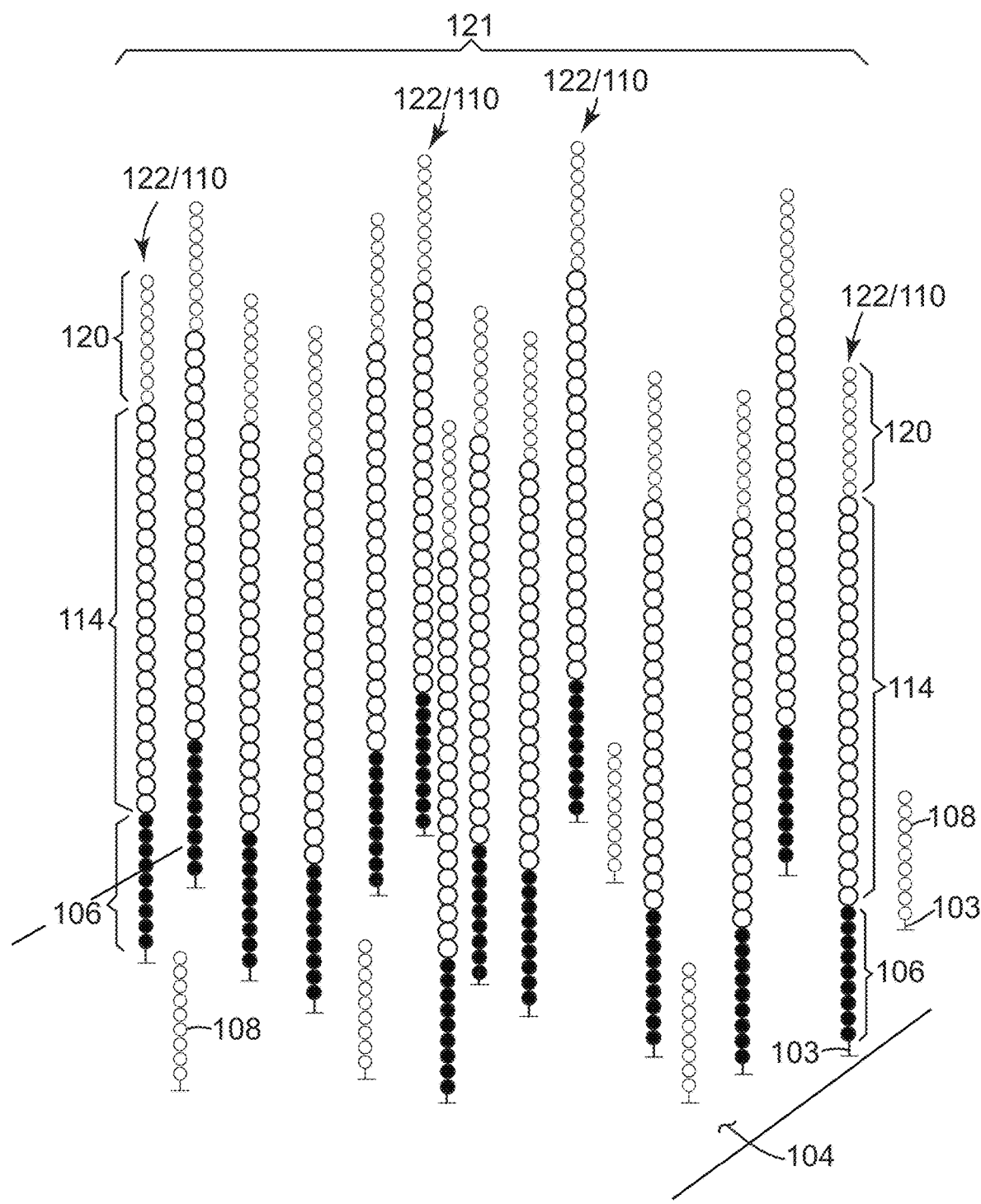
FIG. 3 depicts an example of a cluster of polynucleotide strands attached to a well region as forward strands, according to aspects described herein.

Referring to FIG. 3, an example is depicted of a forward strand cluster 121 of the polynucleotide strands 110 attached to the well region 104 as forward strands 122, according to aspects described herein. When the polynucleotide strand 110 is attached as a forward strand 122, the forward oligo 106 may replace the forward end adapter 118 to anchor to the forward strand 122 to the floor of the well region 104. The reverse end adapter 120 is still tethered to the free end of the forward strand 122.

Figure 4:
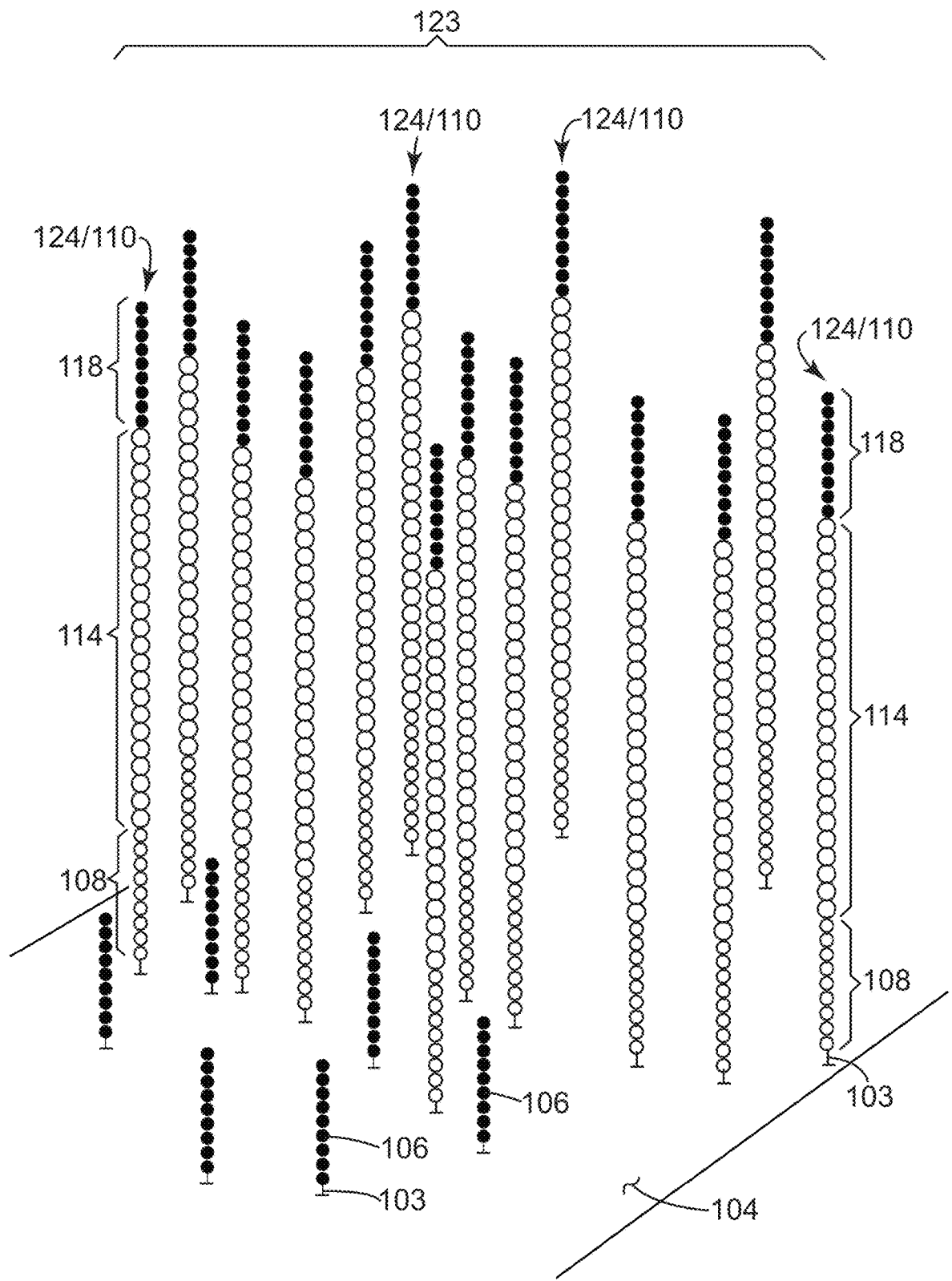
FIG. 4 depicts an example of a cluster of the polynucleotide strands attached to a well region as reverse strands, according to aspects described herein.

Referring to FIG. 4, an example is depicted of a reverse strand cluster 123 of the polynucleotide strands 110 attached to the well region 104 as reverse strands 124, according to aspects described herein. When the polynucleotide strand 110 is attached as a reverse strand 124, the reverse oligo 108 replaces the reverse end adapter 120 to anchor to the strand 110 to the floor of the well region 104. The forward end adapter 118 is still tethered to the free end of the reverse strand 124.

Figure 5:
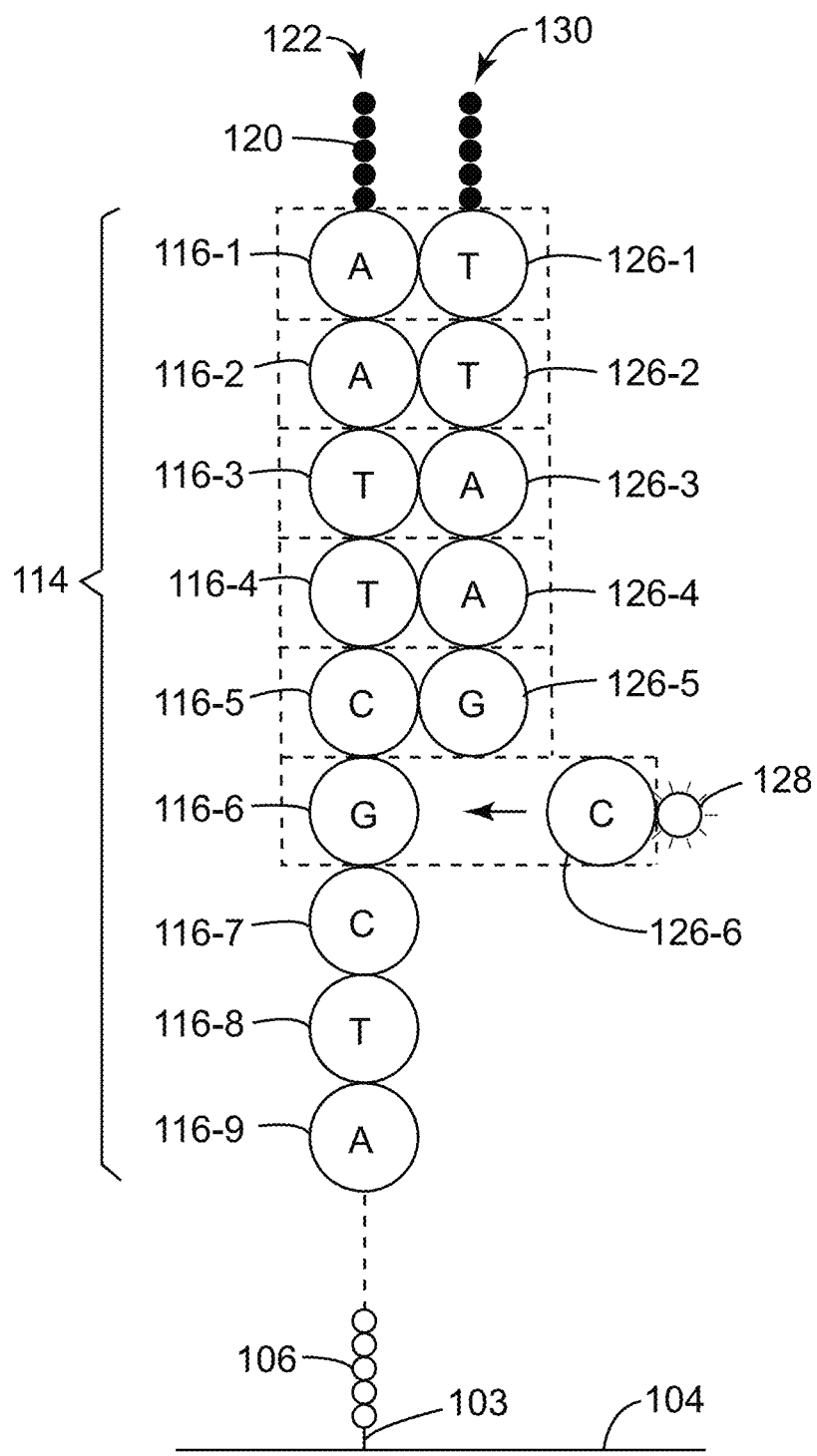
FIG. 5 depicts an example of a forward strand being sequenced to determine the order of its nucleotides, according to aspects described herein.

Referring to FIG. 5, an example is depicted of the forward strand 122 being sequenced to determine the order of its nucleotides 116, according to aspects described herein. The specific type of nitrogenous base associated with each nucleotide 116 (for example, 116-1 through 116-9 and more) of the forward strand 122 is identified by the circled letters A, G, C or T, which represent the base types adenine, guanine, cytosine and thymine respectively of the nucleotide 116.

To identify the sequence of bases of the nucleotides 116 in forward strand 122, a plurality of second nucleotides 126 (for example 126-1 through 126-6 and more), having bases with fluorescent tags 128, are introduced via the flow cell 112 (see FIG. 7A). The bases (A, G, C, T) of nucleotides 126 compete for addition to a growing second polynucleotide 130 that is the complement of the forward strand 122. With each addition of a base of a second nucleotide 126 (for example nucleotide 126-6 having base C and fluorescent tag 128) to the growing second polynucleotide 130 chain, the fluorescent tag 128 is excited via an excitation light. The unique signal of the fluorescent tag 128 identifies the base type of the second nucleotide 126. Once the base is identified, the fluorescent tag 128 is removed. Identifying each second nucleotide 126 of the second polynucleotide 130 also identifies it's associated complementary nucleotide 116 of the forward strand 122. This process of identifying the bases is referred to herein as a "base call."

However, with each cycle of this sequencing process, a degree of uncertainty of each base call increases as the length of the second polynucleotide strand 130 increases. At some point, the degree of uncertainty gets too large to continue. Therefore, in examples where each end of the strand is sequenced serially (that is, not in parallel or at the same time), the forward strand 122 is washed away and the reverse strand 124 is anchored to the well region 104 in place of the forward strand 122. The sequencing process then continues in the same manner on the reverse strand 124.

Figure 6:
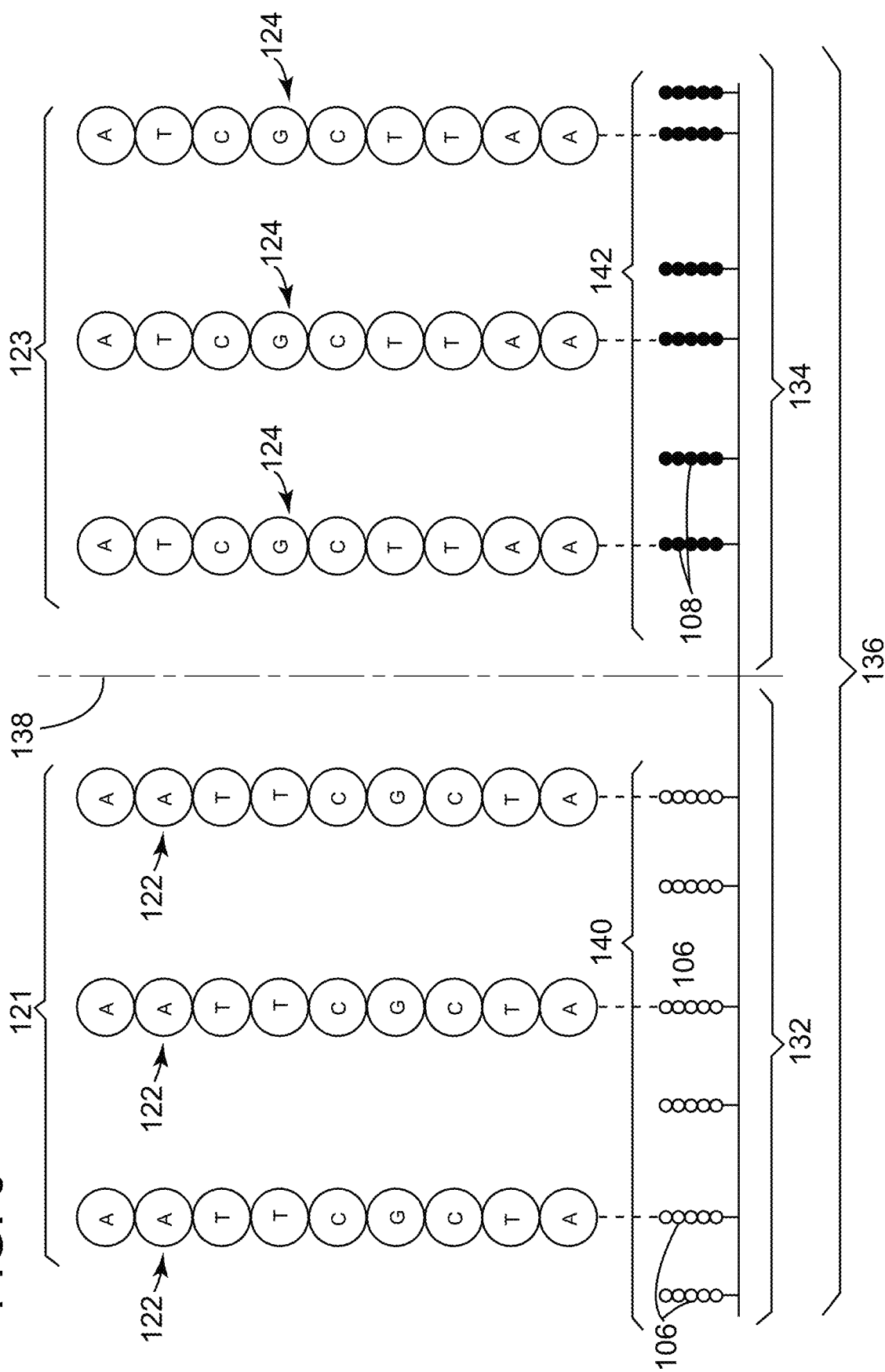
FIG. 6 depicts an example of an adjacent forward strand cluster and reverse strand cluster respectively disposed on a nanowell, according to aspects described herein.

Referring to FIG. 6, an example is depicted of adjacent clusters 121, 123 of the forward strands 122 and reverse strands 124 respectively disposed on a nanowell 136, according to aspects described herein. In this example, the forward and reverse strands 122, 124 are disposed in a first well region 132 and an adjacent second well region 134 of the nanowell 136.

The first and second well regions 132, 134 are separated by a region interface 138. In one example, the region interface 138 is a border line between the two directly adjacent well regions 132, 134. In another example, the region interface 138 has a width that is small enough for clustering to span over the region interface 138 from one well region 132 to the other well region 134.

A first primer set 140 is disposed throughout the first well region 132. A second different primer set 142 is disposed throughout the second well region 134. The difference in the first and second primer sets 140, 142 enables the primer sets to attach the forward strand cluster 121 in the first well region 132 and the reverse strand cluster 123 in the second well region 134. Detailed examples of the differences in the primer sets 140, 142 and the chemistry used to control generation of the forward and reverse strands 122, 124 in the adjacent first and second well regions 132, 134 respectively, are provided in International Patent Application Number PCT/US2019/036105, International Publication Number WO 2020/005503, titled "FLOW CELLS", to Fisher et al., assigned to Illumina, Inc. and having International Filing Date Jun. 6, 2019, which is herein incorporated by reference in its entirety.

In an example of a difference between the first and second primer sets 140, 142, the first primer set 140 may include an un-cleavable first primer and a cleavable second primer. Whereas the second primer set may include a cleavable first primer and an un-cleavable second primer.

In a more specific example, the first primer set 140 may include a first forward oligonucleotide primer 106, with a length of approximately 20 nucleotides, having a specified sequence of adenosine, guanosine, cytidine, and thymidine; and a first reverse oligonucleotide primer 108, with a length of approximately 20 nucleotides, having a different sequence of adenosine, guanosine, cytidine, thymidine and one or more deoxyuridine. The second primer set 142 may include a second forward oligonucleotide primer 106, with a length of approximately 20 nucleotides, having a specified sequence of adenosine, guanosine, cytidine, thymidine, and one or more deoxyuridine; and a second reverse oligonucleotide primer 108, with a length of approximately 20 nucleotides, having a different sequence of adenosine, guanosine, cytidine, thymidine. The N-glycosidic bond at a deoxyuridine site is cleavable by an enzyme. The sequences of the first forward primer 106 in the first primer set 140 and the second forward primer 106 in the second primer set 142 are the same with the exception of a replacement of thymidine with cleavable deoxyuridine. The sequences of the first reverse primer 108 in the first primer set 140 and the second reverse primer 108 in the second primer set 142 are the same with the exception of a replacement of thymidine with cleavable deoxyuridine. Other examples of cleavable nucleosides include those with modified nucleobases, or with linkers including a vicinal diol, a disulfide, a silane, an azobenzene, a photocleavable group, allyl T (a thymine nucleotide analog having an allyl functionality), allyl ethers, or an azido functional ether.

During operation, the first primer set 140 in the first well region 132 is activated to enable a polynucleotide strand 110 to be seeded in the first primer set 140 in the forward position 122. That is, the primer set 140 is available to be hybridized with one or more polynucleotide strands 110. The second primer set 142 is deactivated (for example, by masking the second well region 134, or by not having a seeding primer, or the like) such that no seeding takes place in the second well region 134.

The seeded forward strand 122 is then amplified throughout the first primer set 140 to form a forward strand cluster 121 of forward strands 122 and reverse strands 124 in the first well region 132. The reverse primers 108 are then cleaved out with an enzyme, leaving only forward strands 122 hybridized (attached) to forward primers 106 in the first well region 132.

For purposes herein the term "activated" means: "a means or method of enabling a primer set in a well region to be seeded with a polynucleotide strand (or enable 3'-extension or amplification as alternatives)." The term "deactivated" means the opposite in that it means: "a means or method of disabling a primer set from being seeded with a polynucleotide strand (or disable 3'-extension or amplification as alternatives)." Deactivating a primer set could be accomplished by, for example, masking over a prime set so no polynucleotides could be seeded therein. Alternatively, a primer set could be deactivated by not including a seeding primer in the primer set. Activating a primer set could be accomplished by, for example, unmasking a primer set to expose the primer set to polynucleotide strands that could potentially seed in the well region.

Also, for purposes herein, the term "masking" means: "a means or method of disposing a temporary protective layer over a primer set in a well region to physically prevent access to the primer set by polynucleotide strands." The term "unmasking" means the opposite in that it means: "a means or method of removing a protective layer to expose the primer set to polynucleotide strands for the purposes of seeding."

Also, it is to be understood that amplification and/or sequencing of polynucleotide strands (e.g., forward strands or reverse strands) may not always produce exact duplicates of the strands or exact duplicates of the reverse complements of the strands. This is because, for various factors, errors may be introduced in amplification and/or sequencing process, which may introduce defects (e.g., the incorrect base) in the polynucleotide sequence of bases. For example, there may be up to 1 out of a million defects, 10 out of a million defects or 100 out of a million defects introduced into the sequenced or amplified strands. Accordingly, a cluster of forward or reverse strands 121, 123 may not contain exact duplicates of each strand in the cluster but may include substantially the same duplicates of each strand in the cluster.

Once amplification of the forward strands 122 is substantially complete in the first well region 132, the second primer set 142 is then activated (as by unmasking the second well region 134 or the like) to enable seeding in the second well region 134. For example, any protective layer over the second primer set 142 may be removed (unmasked) to expose both the second forward primers 106 and second reverse primers 108 in the second primer set 142.

Because the first and second well regions 132, 134 are adjacent, the forward strands 122 at the border or region interface 138 can then arch over into the second well region 134 to engage the second primer set 142. The second primer set 142 will then, via bridge amplification, amplify a reverse strand cluster 123 of reverse strands 124 throughout the entire second well region 134. That is, a cluster reaction may then be carried out to form a cluster of forward 122 and reverse strands 124 hybridized to the second forward primers 106 and second reverse primers 108 in the second well region 134. The second forward primers 106 are then cleaved out with an enzyme, leaving only reverse strands 124 hybridized (attached) to second reverse primers 108 in the second well region 134. The result is the forward strand cluster 121 in the first well region 132 and the reverse strand cluster 123 in the second well region 134, as illustrated in FIG. 6.

Advantageously, by providing adjacent clusters 121, 123 of forward strands 122 and reverse strands 124 respectively, simultaneous paired end sequencing (or reading) of adjacent forward strand clusters 121 and reverse strand clusters 123 is enabled. Simultaneous paired-end sequencing allows users to sequence both forward strand 122 and reverse strand 124 types of a polynucleotide strand 110 in parallel and simultaneously, rather than in sequence. This may greatly increase the throughput of the sequencing process described earlier herein. Additionally, or alternatively, this may greatly decrease errors in the sequencing process.

Referring to FIG. 7A, an example is depicted of a cross sectional side view of a sensor system 200 having a flow cell 112 attached to an image sensor structure 100, according to aspects described herein. The image sensor structure 100 is operable to perform simultaneous paired-end sequencing of adjacent forward strand clusters 121 of forward strands 122 and reverse strand clusters 123 of reverse strands 124 as illustrated in FIG. 6.

The flow cell 112 of the sensor system 200 includes a flow cell cover 150 affixed to flow cell sidewalls 152. The flow cell sidewalls 152 may be bonded to a passivation stack 156 of the image sensor structure 100 to form a flow channel 158 therebetween.

The passivation stack 156 includes an array of nanowells 136 disposed thereon. Polynucleotide strands 110 (such as DNA segments, oligonucleotides, other nucleic-acid chains or the like) may be disposed within the nanowells 136 as both forward strand clusters 121 of forward strands 122 and reverse strand clusters 123 of reverse strands 124.

The flow cell cover 150 includes an inlet port 160 and an outlet port 162 that are sized to allow fluid flow 164 into, through and out of the flow channel 158. The fluid flow 164 may be utilized to perform a large number of various controlled reaction protocols on the forward and reverse strands 122, 124 disposed within the nanowells 136. The fluid flow 164 may also deliver nucleotides 126 having fluorescent tags 128 (see FIG. 5) that can be used to tag the polynucleotide strands 122, 124.

The image sensor structure 100 of the sensor system 200 includes an image layer 168 disposed over a base substrate 170. The image layer 168 may be a dielectric layer, such as SiN and may contain an array of light detectors 172 disposed therein. A light detector 172 as used herein may be, for example, a semiconductor, such as a photodiode, a complementary metal oxide semiconductor (CMOS) material, or both. The light detectors 172 detect light photons of emissive light 174 that is emitted from the fluorescent tags 128 attached to the strands 122, 124 in the nanowells 136. The base substrate 170 may be glass, silicon or other like material.

A device stack 176 is disposed over the image layer 168. The device stack 176 may contain a plurality of dielectric layers (not shown) that contain various device circuitry 178 which interfaces with the light detectors 172 and process data signals using the detected light photons.

Also disposed in the device stack 176 is an array of light guides 180. Each light guide 180 is associated with at least one light detector 172 of the array of light detectors. For example, the light guides 180 may be vertically oriented relative to the image layer 168 and positioned directly over its associated light detector 172. Alternatively, the light guides 180 may form an acute angle relative to the image layer 168 and approach its associated light detector 172 from an angle. The light guides 180 direct photons of emissive light 174 from the fluorescent tags 128 on the forward and reverse strands 122, 124 disposed in the nanowells 136 to their associated light detectors 172.

The passivation stack 156, is configured to shield the device stack 176 and light guides 180 from the fluidic environment of the flow cell 112. The passivation stack 156 may be one or more layers. In the example illustrated in FIG. 7A, the passivation stack includes a single passivation layer 182. However, other layers, such as a chemical protection layer (not shown) may also be included in the passivation stack 156. The passivation layer 182 may be composed of silicon nitride (SiN). A chemical protection layer (not shown) may be composed of a tantalum pentoxide ($Ta_2O_5$).

The array of nanowells 136 is disposed in the passivation stack 156, wherein each nanowell 136 of the array of nanowells is associated with at least one light guide (a first light guide) 180A of the array of light guides 180. In the example illustrated in this FIG. 7A, each nanowell 136 is associated with a first light guide 180A and a second light guide 180B.

As illustrated in FIG. 6, a first primer set 140 is disposed throughout a first well region 132 of each nanowell 136. A different second primer set 142 is disposed throughout a second well region 134 of each nanowell 136. The second well region 134 is adjacent to the first well region 132 at the region interface 138. The first and second primer sets 140, 142 are operable to attach a forward strand cluster 121 of forward polynucleotide strands 122 in the first well region 132 and to attach an adjacent reverse strand cluster 123 of reverse polynucleotide strands 124 in the second well region 134.

The first and second well regions 132, 134 may be positioned over portions of a single light guide 180A. However, in the example illustrated in FIG. 7A, the first well region 132 is disposed over the first light guide 180A and the second well region 134 is disposed over the second light guide 180A.

During operation, various types of excitation light 186 is radiated onto the forward and reverse strands 122, 124 in the nanowells 136, causing the fluorescent tags 128 to fluoresce emissive light 174. The majority or substantial amount of photons of emissive light 174 may be transmitted through the passivation stack 156 and enter its associate light guide 180A, 180B. The light guides 180 may filter out most of the excitation light 186 and direct the emissive light 174 to an associated light detector 172 located directly below the light guide 180.

The examples illustrated herein show excitation light 186 being radiated from a front side of the image sensor structure 100 to excite the fluorescent tags 128 and fluoresce emissive light 174. However, it is within the scope of this disclosure that excitation light 186 may be radiated from a back side of the image sensor structure (i.e., back-side illumination) to excite the fluorescent tags 128 and fluoresce emissive light 174.

The light detectors 172 detect the emissive light photons. The device circuitry 178 within the device stack 176 then converts the detected emissive light photons to data signals, which are transmitted electrically to external readout devices. The data signals may then be analyzed to simultaneously reveal the order of nucleotides of both the forward strands 122 and reverse strands 124.

Referring to FIG. 7B, an example is depicted of a top view of the image sensor structure of FIG. 7A taken along the line 7B-7B of FIG. 7A, according to aspects described herein. In the example of FIG. 7B, the first and second well regions 132, 134 are substantially equal in area and directly adjacent to each other at well region 138. The well regions are rectangular in shape because the floor 185 of the nanowells 136 is rectangular. Each well region 132, 134 is substantially centered over its associated light guide 180A and 180B.

Except at the region interface 138, the first well region 132 may be bounded by a wall 181 of the nanowell 136. Also except at the interface region 138, the second well region 134 may be bounded by a wall 183 of the nanowell 136. Essentially throughout the image sensor structure 100, multiple paired first and second well regions 132, 134 may be defined by walls 181, 183 of the nanowells 136.

However, because the nanowells 136 span two light guides 180A, 180B, there is a greater risk of polyclonality in the two well regions as compared to nanowells that span only one light guide. That is, there is a greater risk of more than one type of polynucleotide strand 110 (see FIG. 2) entering the nanowell 136 simultaneously and seeding and amplifying together, therefore significantly increasing the signal to noise ratio.

Additionally, the region interface 138 spans across the entire largest width (represented by arrow 188) of the first and second well regions 132, 134. Therefore, there is an increased risk of crosstalk from the reverse strands 124 (especially reverse strands at the large border/region interface 138) entering the light guide 180A and contaminating the signals from the forward strands 122.

Figure 8:
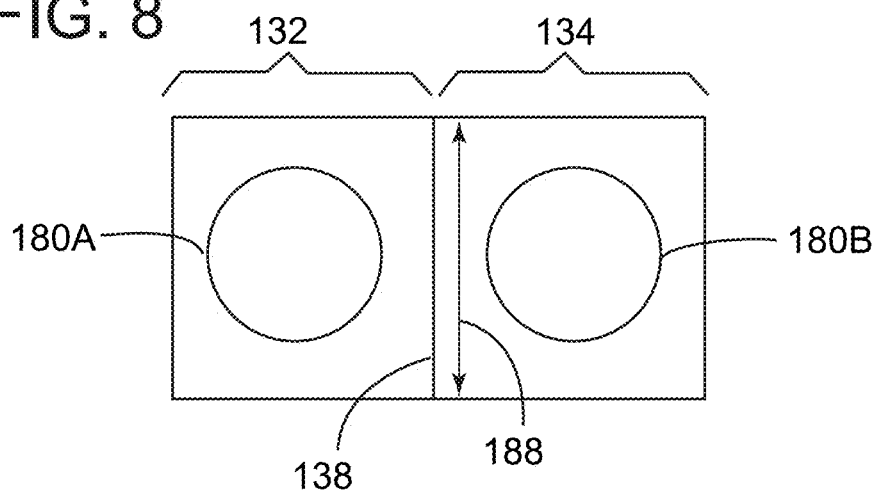
FIG. 8 depicts an example of a top view of a first well region and an adjacent second well region in a nanowell of an image sensor structure, wherein the first and second well regions have substantially equal areas, according to aspects described herein.

Referring to FIG. 8, an example is depicted of a top view of the first well region 132 and the adjacent second well region 134 in the nanowell 136 of the image sensor structure 100, wherein the first and second well regions 134, 136 have substantially equal areas, according to aspects described herein. FIG. 8 is essentially an enlarged view of the first and second well regions 132, 134 of FIG. 7B. The rectangular area of well region 132 extends beyond the circular boundary of the light guide 180A. Much of the area beyond the circular boundary of the light guide 180A may not be required for a strong signal from the forward strands 122 that are amplified in well region 132.

Figure 9:
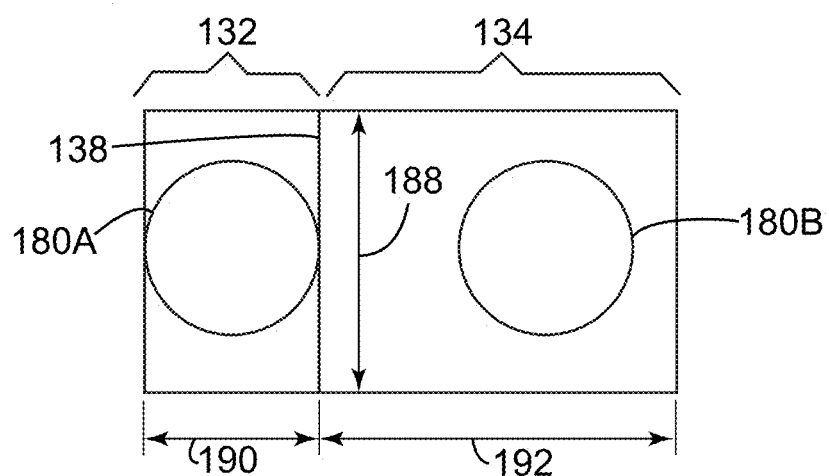
FIG. 9 depicts another example of a top view of a first well region and an adjacent second well region in a nanowell of an image sensor structure, wherein the first and second well regions have substantially unequal areas, according to aspects described herein.

Referring to FIG. 9, another example is depicted of a top view of a first well region 132 and an adjacent second well region 134 in a nanowell 136 of an image sensor structure 100, wherein the first and second well regions have substantially unequal areas, according to aspects described herein. In FIG. 9, the area of the first well region 132 is smaller than the area of the second well region 134. Since the rectangular areas of first and second well regions 132, 134 have substantially equal width 188, then by changing the length of first well region 132 (designated by arrow 190) and the length of second well region 134 (designated by arrow 192) the areas are made to change. In this case, the length of 190 of region 132 is made shorter than the length 192 of region 134, so the area of region 132 is made smaller than the area of region 134.

For example, the first and second well regions 132, 134 may have substantially equal widths 188, and the first well region 132 may have a length 190 that is 90% or less of a length 192 of the second region 134. Note that in this example, the length 190 is not so small that the first well region does not fully cover its associated light guide 180A. Positioning the forward strands 122 associated with first well region 132 entirely over the light guides 180A helps to produce a strong signal at the light detector 172 even though the area of the well region 132 has been reduced.

By reducing the area of first well region 132, the risk of unwanted polyclonality goes down. Further, the second well region is not activated until after the forward strands 122 have been fully amplified and no polynucleotides are being flowed through the flow channel 158. Accordingly, very little if any polyclonality will carry over into the second well region from the first well region once the reverse strands 124 begin to amplify in the second well region 134.

Figure 10:
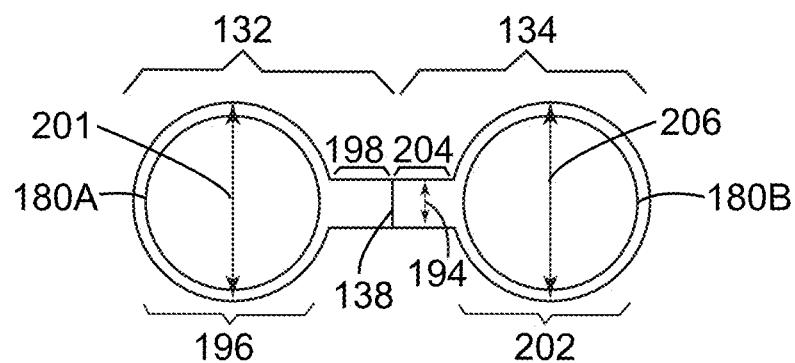
FIG. 10 depicts another example of a top view of a first well region and an adjacent second well region in a nanowell of an image sensor structure, wherein the first and second well regions have a generally dog-bone shape, according to aspects described herein.

Referring to FIG. 10, another example is depicted of a top view of a first well region 132 and an adjacent second well region 134 in a nanowell 136 of an image sensor structure 100, wherein the first and second well regions 132, 134 have a generally dog-bone shape, according to aspects described herein. The dog-bone shape reduces the areas of the well regions 132, 134, which helps to reduce polyclonality, but provides physical continuity between the two well regions 132, 134 so as to permit cluster growth between them. Additionally, the smaller the width 194 of the dog-bone at the interface region 138, the less crosstalk that can occur. This is because, the walls of the nanowell 136 on either side of the neck of the dog bone, may function to help block cross talk from the larger circular areas.

In the dog-bone shape, the first well region 132 includes a first section 196 and a second section 198. The first section 196 is disposed over the entire first light guide 180A. This helps to ensure a strong signal to the light guide 180A.

The first section 196 has a first section width 201. Note that the first section 196 does not have to be circular. Rather, the first section may be square, rectangular or any other appropriate shape.

The second section 198 extends from the first section 196 to the region interface 138. The second section 198 has a second section width 194 that is less than the first section width 201.

The second well region 134 includes a third section 202 and a fourth section 204. The third section 202 is disposed over the entire second light guide 180B. This helps to ensure a strong signal to the light guide 180B.

The third section 202 has a third section width 206. Note that the third section 202 does not have to be circular. Rather, the third section may be square, rectangular or any other appropriate shape.

The fourth section 204 extends from the first section 202 to the region interface 138. The fourth section 204 has a fourth section width 194 that is less than the third section width 206. Note that in this example, the second section 198 width 194 of the first well region 132 and the fourth section 204 width 194 of the second well region 134 are substantially equal. Also, in this example, the length of the second section 198 of the first well region 132 and the fourth section 204 of the second well region 134 are substantially equal. In other examples, the length of the second section 198 of the first well region 132 and the fourth section 204 of the second well region 134 are substantially unequal.

In some examples, the first section 196 and third section 202 having substantially circular shapes. That being the case, then the first and third section widths 201, 206 are diameters of the first and third sections 196, 202 respectively. In some examples, the second and fourth section widths 194 are 50% or less than the first and third section widths 201, 206 respectively.

Figure 11:
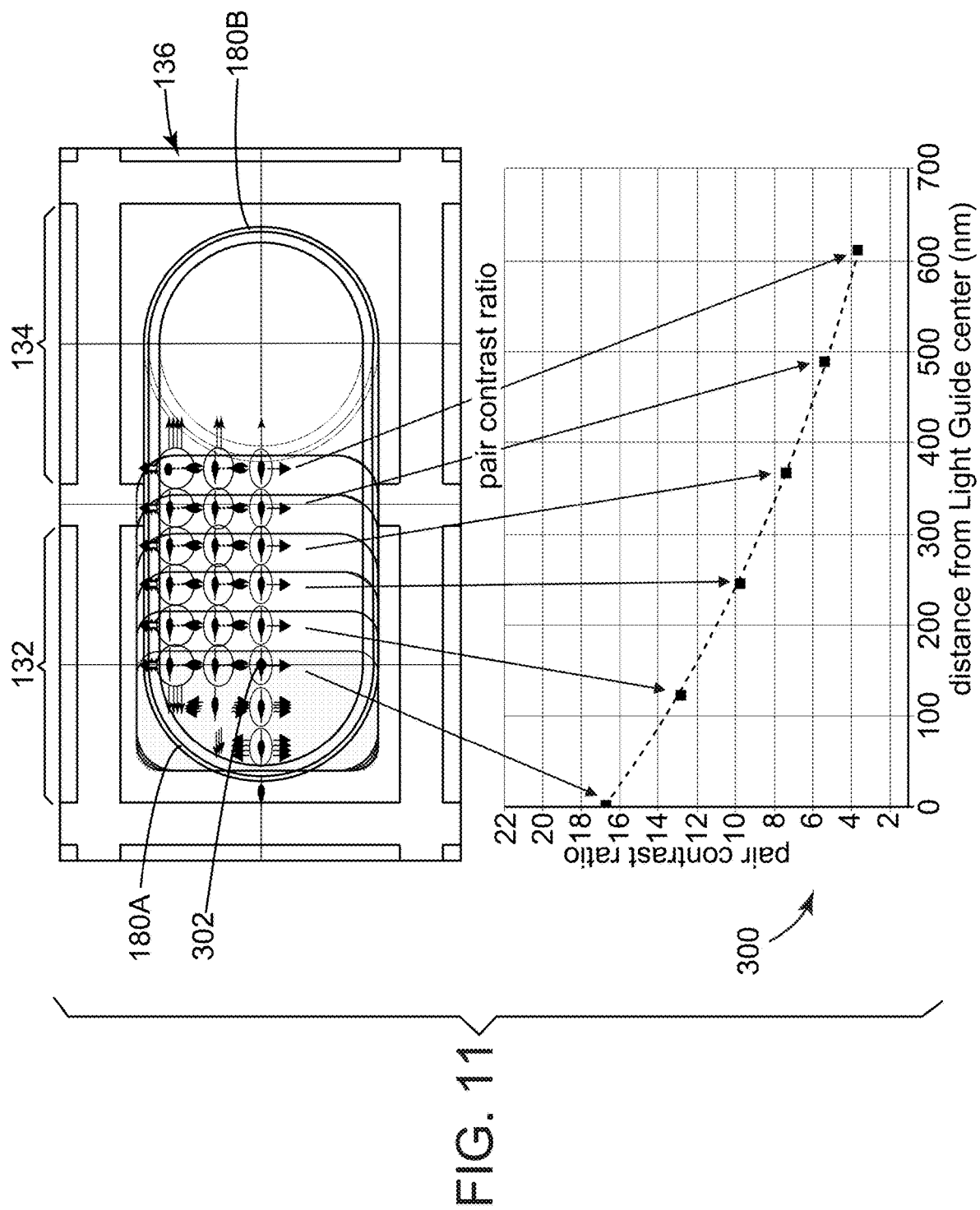
FIG. 11 depicts an example of a graph of pair (first well region having a forward strand cluster and second well region having a reverse strand cluster) contrast ratio vs distance from a light guide center associated with the first well region, according to aspects described herein.

Referring to FIG. 11, an example is depicted of a graph 300 of pair (first well region 132 having a forward strand cluster 121 and second well region 134 having a reverse strand cluster 123) contrast ratio vs distance from a light guide center 302 associated with the first well region 132, according to aspects described herein. Contrast ratio is defined as follows:

Contrast ratio=the signal received at the first light guide 180A from region 132 (i.e., the brightest signal A) divided by the signal received at the first light guide 180A from the adjacent region 134 (i.e., the second brightest signal B).

If: A=the brightest signal, and B=the second brightest signal, then the contrast ratio may be written as: Contrast ration=A/B The contrast ratio is closely related to the chastity score, which may be defined as Chastity=A/(A+B).

Therefore, if the contrast ratio is 5 to 1, the chastity score equals 5/(5+1)=83%.

Both contrast ratio and chastity score are concerned with the overall purity of the fluorescent signal at the base of the target area. That is the area that is targeted to be measured.

The graph 300 shows that as the first well region 132 gets longer and larger in area (i.e., grows further away from the center of its associated light guide 180A), the contrast ratio and chastity score grow smaller. Therefore, it would seem that the smaller an area for a well region 132, the purer the signal and the less crosstalk.

However, this must be balanced by the fact that as the area of well region 132 gets smaller, the less amplified the signal from that area becomes and the more the signal from the adjacent well region 134 gets amplified. Accordingly, if a well region gets too small, it could be overwhelmed by the brightness of the adjacent well region.

Figure 12:
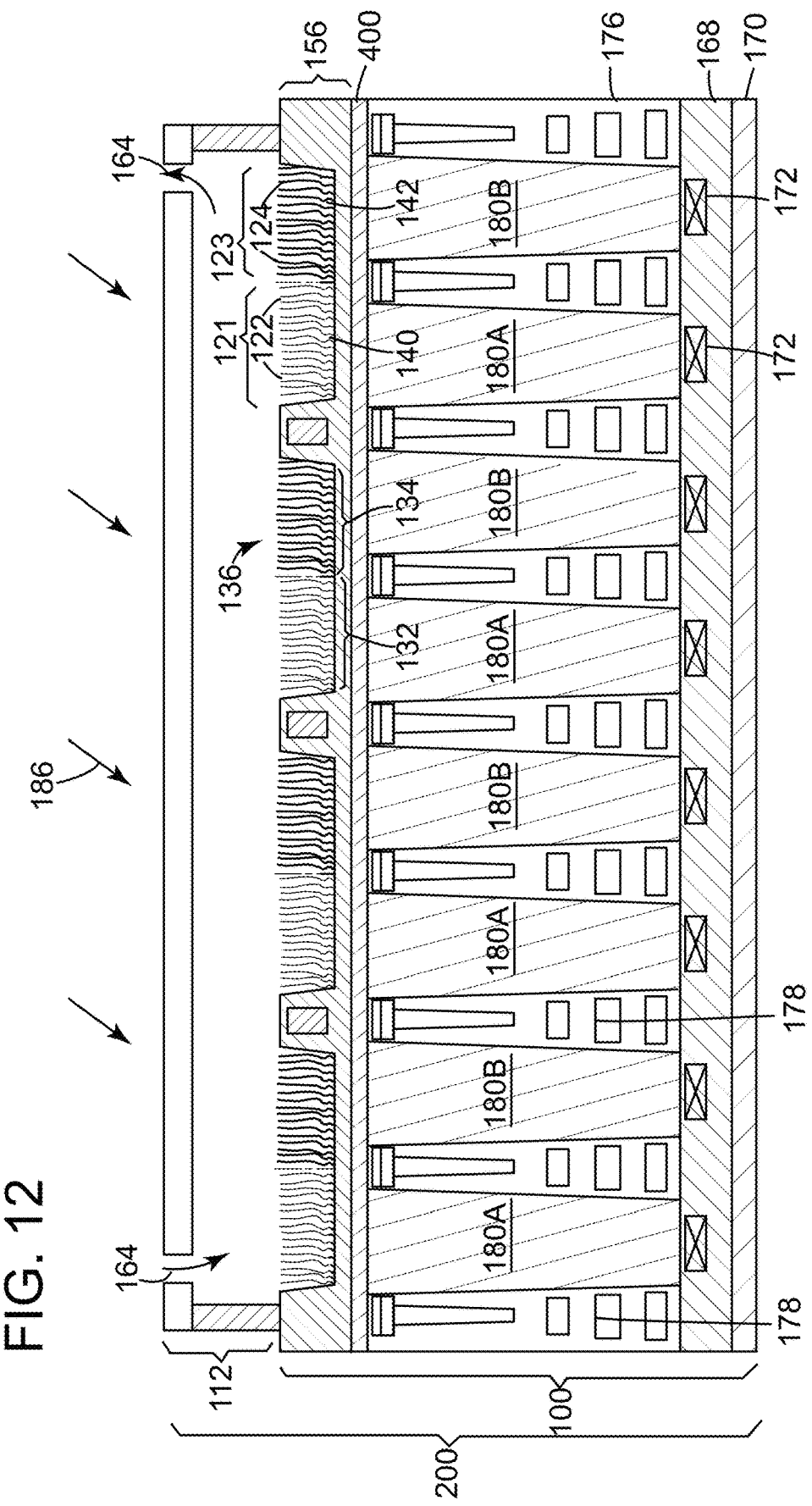
FIG. 12 depicts an example of a cross sectional view of an image sensor structure having an opaque layer disposed between an array of light guides and first and second well regions of a nanowell, according to aspects describe herein.

Referring to FIG. 12, an example is depicted of a cross sectional view of an image sensor structure 100 having an opaque layer 400 disposed between an array of light guides 180 and first and second well regions 132, 134 of a nanowell 136, according to aspects describe herein. FIG. 12 is substantially the same as FIG. 7, except for the addition of the opaque layer 400 positioned between the passivation stack 156 and the light guides 180. In some examples, the opaque layer may be composed of tantalum, chrome, titanium, aluminum or the like. As used herein, the term "opaque" means blocking all or substantially all light or radiant energy of one or more ranges of wavelengths or all wavelengths from passing therethrough.

Figure 13A:
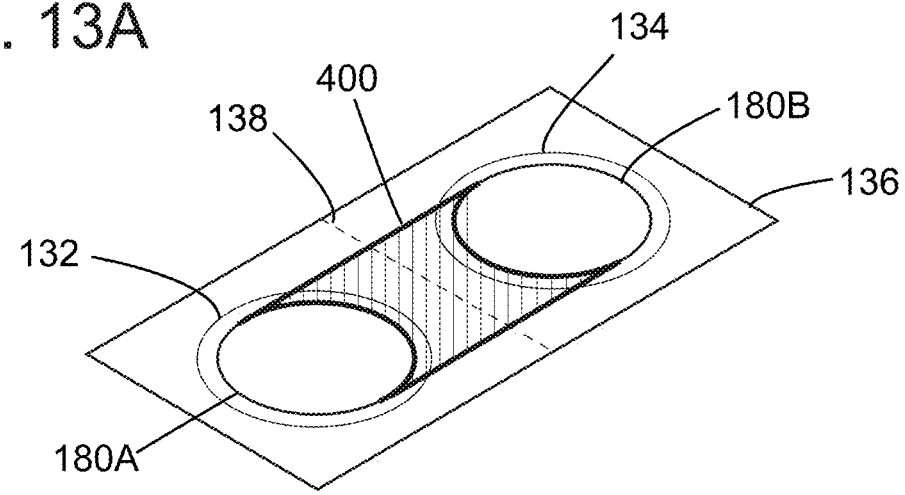
FIG. 13A depicts an example of a top perspective view of the opaque layer of the image sensor structure of FIG. 12, according to aspects described herein.
Figure 13B:
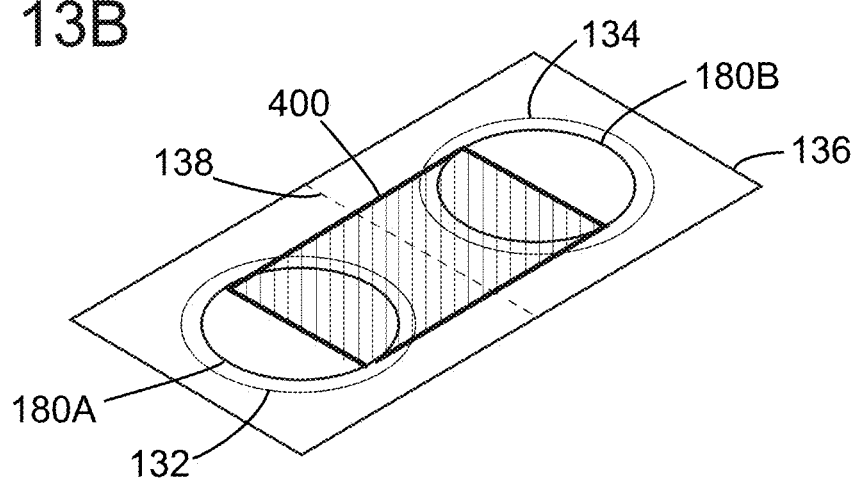
FIG. 13B depicts another example of a top perspective view of the opaque layer of the image sensor structure of FIG. 12, according to aspects described herein.
Figure 13C:
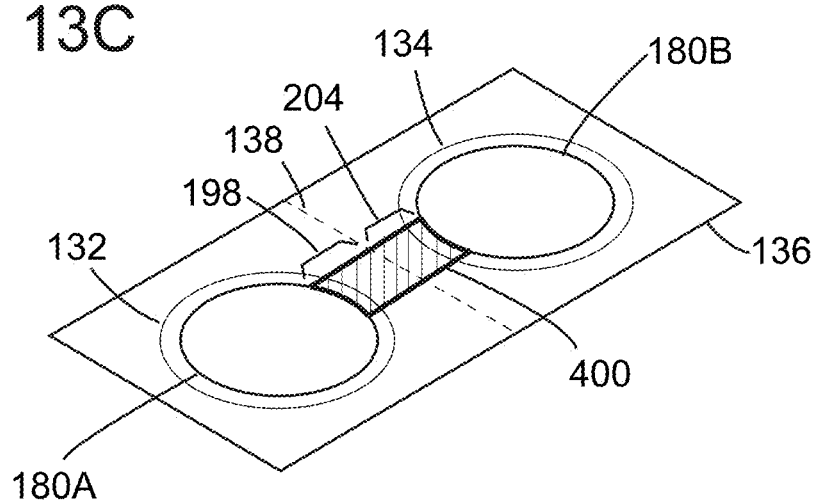
FIG. 13C depicts another example of a top perspective view of the opaque layer of the image sensor structure of FIG. 12, according to aspects described herein.

Referring to FIGS. 13A, 13B and 13C, three different examples are depicted of a top perspective view of the opaque layer 400 of the image sensor structure of FIG. 12, according to aspects described herein. In each case of the three configurations of opaque layers depicted in FIGS. 13A-C, the opaque layer 400 is disposed between the array of light guides 180 and the first and second well regions 132, 134 of each nanowell 136. Further, each configuration of the opaque layer 400 extends under the entire region interface 138 of the first and second well regions 132, 134. Additionally, each opaque layer 400 depicted covers less than an entire portion of top surfaces of the first and second light guides 180A, 180B associated with each nanowell 136.

Because the first and second well regions 132, 134 are adjacent at region interface 138, the bulk of the cross talk occurs in that area. Accordingly, the opaque layer 400 is placed across the entire interface area 138 for the purpose of reducing such cross talk.

Specifically, in FIG. 13A, the opaque layer 400 does not cover any portion of the top surfaces of first and second light guides 180A, 180B associated with each nanowell 136. Rather the opaque layer 400 follows the perimeters of each first and second light guides 180A, 180B.

Specifically, in FIG. 13B, the opaque layer 400 does covers a portion of the top surface of the first and second light guides 180A, 180B. For example, the opaque layer 400 may cover greater than 10%, greater than 15% or greater than 25% of the top surfaces of the first and second light guides 180A, 180B associated with each nanowell 136.

Specifically, in FIG. 13C, the opaque layer 400 covers the neck sections of a dog bone shaped first and second well regions 132, 134, but does not cover any portion of the first and second light guides 180A, 180B. That is, the opaque layer 400 covers the second section 198 of the first well region 132 and the fourth section 204 of the second well region 134, but follows the perimeter of the light guides 180A, 180B.

Figure 14A:
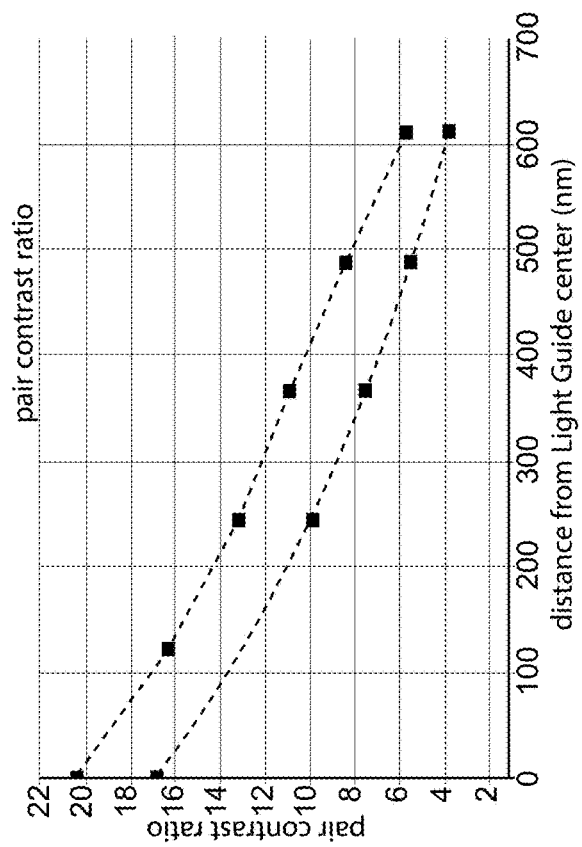
FIG. 14A depicts an example of a graph of pair contrast ratio vs distance from a light guide center associated with the first well region, wherein no opaque layer is disposed between the first and second well regions and the array of light guides, according to aspects described herein.

Referring to FIGS. 14A, an example is depicted of a graph 500 of pair contrast ratio vs distance from a light guide center associated with the first well region 180A, wherein no opaque layer 400 is disposed between the first and second well regions 132, 134 and the array of light guides 180, according to aspects described herein.

Figure 14B:
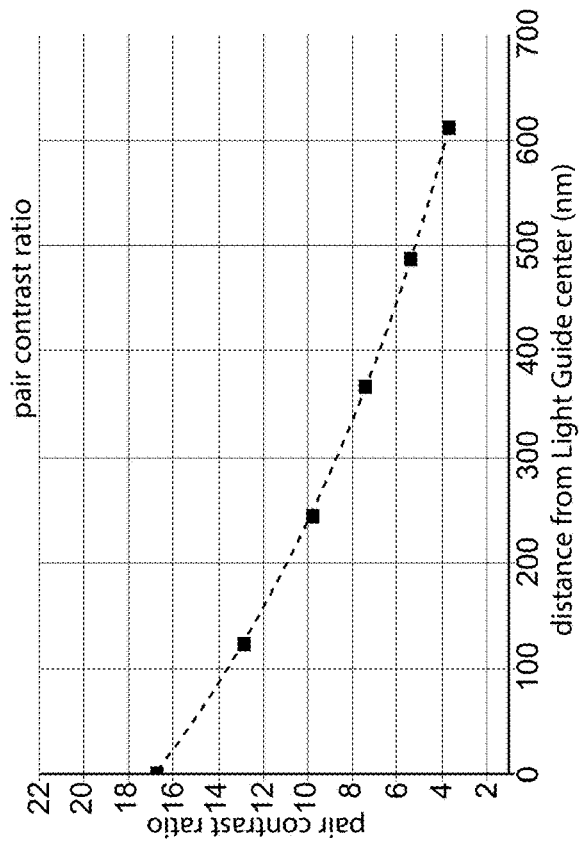
FIG. 14B depicts an example of a graph of pair contrast ratio vs distance from a light guide center associated with the first well region, wherein an opaque layer is disposed between the first and second well regions and the array of light guides, according to aspects described herein.

Referring also to FIG. 14B, an example is depicted of a graph 502 of pair contrast ratio vs distance from a light guide center associated with the first well region 180A, wherein an opaque layer 400 is disposed between the first and second well regions 132, 134 and the array of light guides 180, according to aspects described herein.

The graph 500 is substantially the same as graph 300, wherein the pair contrast ratio vs. distance from the center of light guide 180A is plotted. Graph 502 plots the same parameters, except that the image sensor structure 100 now includes an opaque layer 400. As can be seen by comparing the two graphs 500, 502, the contrast ratio improves substantially with the opaque layer. This improvement is due in large part to the fact that the opaque layer 400 is placed across the entire region interface area 138, where the bulk of the cross talk takes place.

Figure 15:
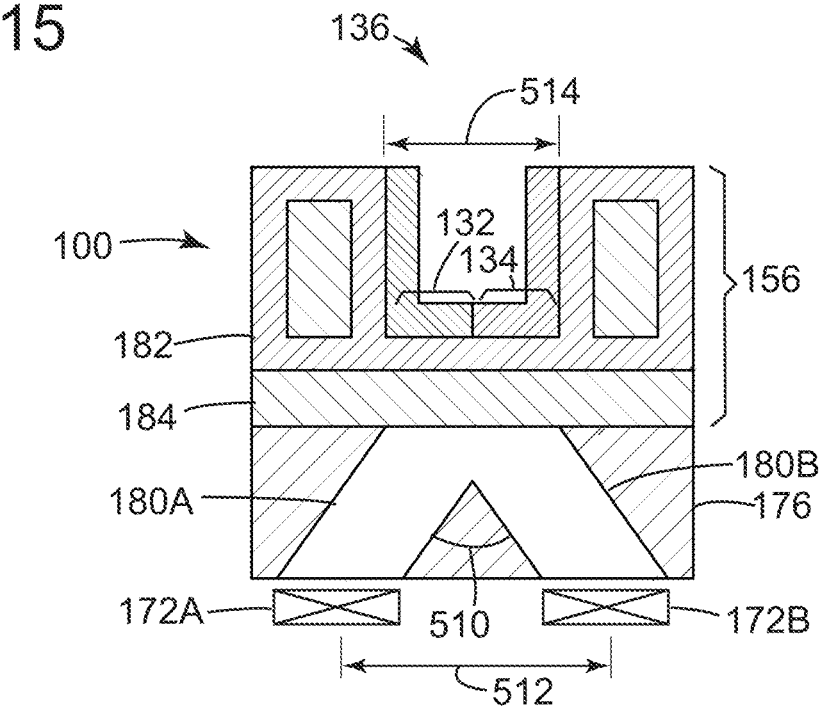
FIG. 15 depicts an example of a cross sectional view of an image sensor structure having first and second well regions disposed over first and second light guides, wherein the light guides form an acute angle relative to each other, according to aspects described herein.

Referring to FIG. 15 an example is depicted of a cross sectional view of an image sensor structure 100 having first and second well regions 132, 134 disposed over first and second light guides 180A, 180B, wherein the light guides 180A, 180B form an acute angle 510 relative to each other, according to aspects described herein. In this example, the passivation stack 156 includes two layers, a first passivation layer 182 and a chemical protection layer. The first and second light guides 180A, 180B are disposed in the device stack 176 and angle down to their associated light detectors 172.

Because the pitch 512 between light detectors 172 can only be made so small, it becomes a limiting factor in how small the nanowells 136 can be when they span two light detectors 172. In the example depicted in FIG. 15, the nanowell 136 can be made smaller than the pitch 512 between light detectors 172 due to the angle 510.

Accordingly, the image sensor structure 100 of FIG. 15 includes the first light guide 180A associated with a first light detector 172A of the array of light detectors 172. The second light guide 180B is associated with a second light detector 172B of the array of light detectors 170. Each nanowell 136 associated with the first and second light guides 180A, 180B has a width 514 that is less than the pitch 512 between the first and second light detectors 172A, 172B. The first and second light guides 180A, 180B extend from their associated nanowell 136 to their associated first and second light detectors 172A, 172B at an acute angle 510 relative to each other.

Figure 16:
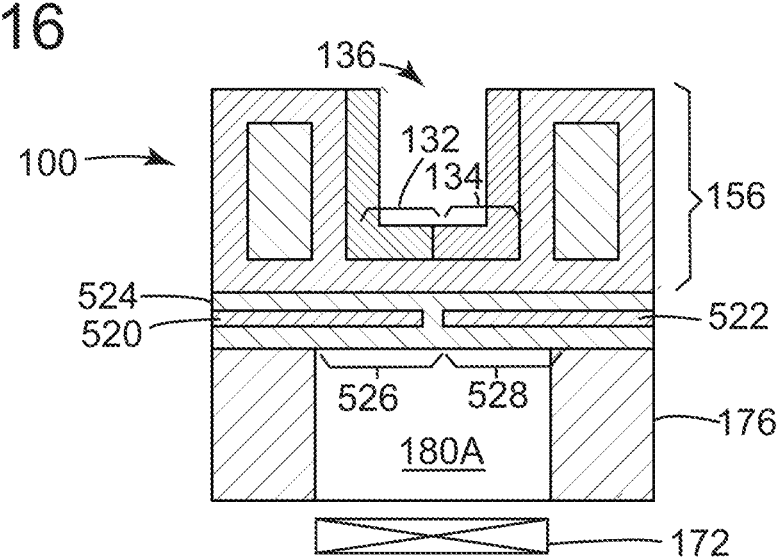
FIG. 16 depicts an example of a cross sectional view of an image sensor structure having a nanowell with first and second well regions disposed over first and second portions of a light guide, wherein first and second waveguides are disposed in a waveguide layer and extend under the first and second well regions respectively, according to aspects described herein.

Referring to FIG. 16, an example is depicted of a cross sectional view of an image sensor structure 100 having a nanowell 136 with first and second well regions 132, 134 disposed over first and second portions 526, 528 of a first light guide 180A associated with the nanowell 136, wherein first and second waveguides 520, 522 are disposed in a waveguide layer 524 and extend under the first and second well regions 132, 134 respectively, according to aspects described herein.

The nanowell 136 of FIG. 16, and its corresponding structure, may be indicative of an array of nanowells 136 that are disposed within a passivation stack 156 and over a device stack 176 of the image sensor structure 100. The device stack 176 may include an array of light guides 180 disposed therein. Each nanowell 136 may be associated with a first light guide 180A of the array of light guides 180. Each first light guide 180A may be associated with a light detector 172 of an array of light detectors 172.

The image sensor structure 100 of FIG. 16 includes the first well region 132 disposed over a first portion 526 of the associated first light guide 180A. The second well region 134 is disposed over a second portion 528 of the associated first light guide 180A. A waveguide layer 524 is disposed between the array of light guides 180 and the first and second well regions 132, 134 of each nanowell 136. A first waveguide 520 is disposed in the waveguide layer 524 and extends under the first well region 132. The first waveguide 520 is operable to illuminate excitation light on a forward strand cluster 121 of forward polynucleotide strands 122 attached in the first well region 132. A second waveguide 522 is disposed in the waveguide layer 524 and extends under the second well region 134. The second waveguide 522 is operable to illuminate excitation light on a reverse strand cluster 123 of reverse polynucleotide strands 124 attached in the second well region 134.

The first and second waveguides 522, 524 may illuminate the first and second well regions 132, 134 serially. In that way, the first waveguide 520 may excite primarily forward strands 122 attached in the first well region 132, which may be read by the light detector 172. Thereafter, the second waveguide 522 may excite primarily reverse strands 124 attached in the second well region 134, which may also be read by the same light detector 172. In this way, the nanowell 136 would not have to span two light detectors and may be made substantially smaller for improved polyclonality.

During operation, when excitation light 186 is passed through the first waveguide 520, most of the excitation light is focused on the forward strands 122 of the forward strand cluster 121 in the first well region 132. However, at least some of the excitation light 186 from the first wave guide 520 may be incident on the reverse strand cluster 123 in the second well region 134. Accordingly, though the emissive light 174 read by the light detector 172 may be radiated primarily from the forward strands 122 in the first well region 132, a smaller percentage (e.g. less than 25%, less than 15% or less than 10%) of emissive light 174 read by the light detector 172 may be radiated from reverse strands 124 in the second well region 134.

Also, during operation, when excitation light 186 is passed through the second waveguide 522, most of the excitation light is focused on the reverse strands 124 of the reverse strand cluster 123 in the second well region 134. However, at least some of the excitation light 186 from the second wave guide 522 may be incident on the forward strand cluster 121 in the first well region 132. Accordingly, though the emissive light 174 read by the light detector 172 may be radiated primarily from the reverse strands 124 in the second well region 134, a smaller percentage (e.g., less than 25%, less than 15% or less than 10%) of emissive light 174 read by the light detector 172 may be radiated from forward strands 122 in the first well region 132.

Figure 17:
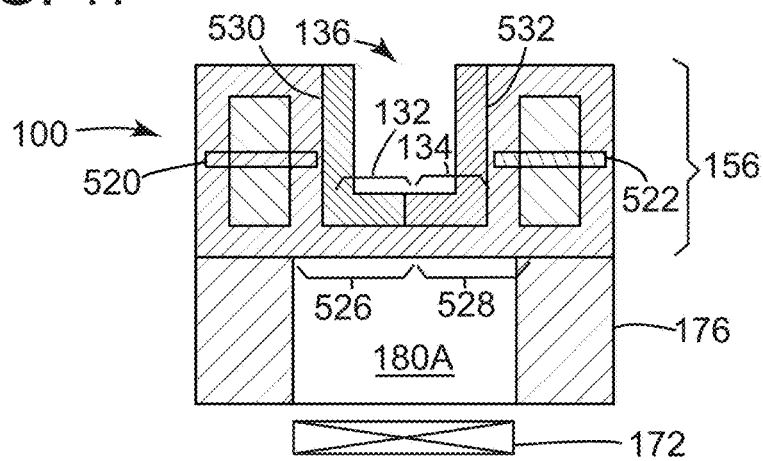
FIG. 17 depicts an example of a cross sectional view of an image sensor structure having a nanowell with first and second well regions disposed over first and second portions of a light guide, wherein first and second waveguides are disposed in a passivation stack adjacent to, and on opposing sides of, the nanowell, according to aspects described herein.

Referring to FIG. 17, an example is depicted of a cross sectional view of an image sensor structure 100 having a nanowell 136 with a first well region 132 and a second well region 134 disposed over first and second portions 526, 528 respectively of a light guide 180A. In the example depicted, a first waveguide 520 and a second waveguides 522 are disposed in a passivation stack 156. The first and second waveguides 520, 522 are positioned adjacent to, and on, opposing sides of 530, 532 of the nanowell 136.

The nanowell 136 of FIG. 17, and its corresponding structure, may be indicative of an array of nanowells 136 that are disposed within a passivation stack 156 and over a device stack 176 of the image sensor structure 100. The device stack 176 may include an array of light guides 180 disposed therein. Each nanowell 136 may be associated with a first light guide 180A of the array of light guides 180. Each first light guide 180A may be associated with a light detector 172 of an array of light detectors 172.

The combination of examples illustrated in FIGS. 16 and 17 indicate that the first and second waveguides 520, 522 may be positioned anywhere in the image sensor structure 100 above (or over) the device stack 176. For example, the waveguides 520, 522 of FIG. 16 are disposed in a waveguide layer 524, which is disposed over the device stack 176. Also by way of example, the waveguides 520, 522 of FIG. 17 are disposed in the passivation stack 156, wherein the passivation stack 156 is positioned over the device stack 176 and forms the walls of the nanowells 136.

Moreover, the first and second waveguides 520, 522 may be indicative of arrays of first and second wave guides 520, 522. More specifically, an array of first waveguides 520 may be disposed over the device stack 176, wherein each first waveguide 520 may be associated with a nanowell 136 of the array of nanowells 136. Each first waveguide 520 may be operable to illuminate excitation light on a forward strand cluster 121 (see FIG. 6) of forward polynucleotide strands 122 attached in the first well-region 132 of the first waveguide's associated nanowell 136.

Also more specifically, an array of second waveguides 522 may be disposed over the device stack 176, wherein each second waveguide 522 may be associated with a nanowell 136 of the array of nanowells 136. Each second waveguide 522 may be operable to illuminate excitation light on a reverse strand cluster 123 (see FIG. 6) of reverse polynucleotide strands 124 attached in the second well-region 134 of the second waveguide's associated nanowell 136.

During operation, when excitation light 186 is passed through the first waveguide 520 positioned adjacent side 530 of nanowell 136, most of the excitation light is focused on the forward strands 122 of the forward strand cluster 121 in the first well region 132. However, at least some of the excitation light 186 from the first wave guide 520 may be incident on the reverse strand cluster 123 in the second well region 134. Accordingly, though the emissive light 174 read by the light detector 172 may be radiated primarily from the forward strands 122 in the first well region 132, a smaller percentage (e.g. less than 25%, less than 15% or less than 10%) of emissive light 174 read by the light detector 172 may be radiated from reverse strands 124 in the second well region 134.

Also, during operation, when excitation light 186 is passed through the second waveguide 522 positioned adjacent side 532 of nanowell 136, most of the excitation light is focused on the reverse strands 124 of the reverse strand cluster 123 in the second well region 134. However, at least some of the excitation light 186 from the second wave guide 522 may be incident on the forward strand cluster 121 in the first well region 132. Accordingly, though the emissive light 174 read by the light detector 172 may be radiated primarily from the reverse strands 124 in the second well region 134, a smaller percentage (e.g., less than 25%, less than 15% or less than 10%) of emissive light 174 read by the light detector 172 may be radiated from forward strands 122 in the first well region 132.

Figure 18:
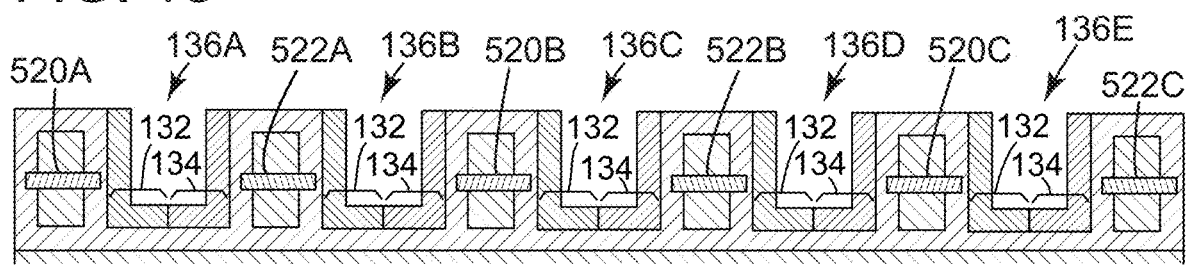
FIG. 18 depicts an example of a cross sectional view of an image sensor structure having an array of the nanowells and the light guides of FIG. 17, according to aspects described herein.

Referring to FIG. 18, an example is depicted of a cross sectional view of an image sensor structure 100 having an array of the nanowells 136 (individually 136A-E) and an array of first light guides 520 (individually 520A-C) and second light guides 522 (individually 522A-C). Each first and the second light guide 520, 522 of the array of first and second light guides 520, 522 have the same or similar structure as the first and second light guides as illustrated in FIG. 17.

Each first waveguide 520 of the array of first waveguides 520 is operable to illuminate excitation light on a cluster 121 or 123 of polynucleotide strands 122 or 124 attached in the first or second well-region 132 or 134 of a nanowell 136 adjacent to the first waveguide's associated nanowell 136 (see FIG. 6). Additionally, each second waveguide 522 of the array of second waveguides 522 is also operable to illuminate excitation light on a cluster 121 or 123 of polynucleotide strands 122 or 124 attached in the first or second well-region 132 or 134 of a nanowell 136 adjacent to the second waveguide's associated nanowell 136 (see FIG. 6).

As an illustrated example, the nanowell 136A in FIG. 18 would be associated with first and second waveguides 520A and 522A. However, second waveguide 522A would also be operable to illuminate excitation light on a forward cluster 121 of forward polynucleotide strands 122 attached to the first well region 132 of the adjacent nanowell 136B.

Also by way of example, the nanowell 136B in FIG. 18 would be associated with first and second waveguides 520B and 522A. However, first waveguide 520B would also be operable to illuminate excitation light on a forward cluster 121 of polynucleotide strands 122 attached to the first well region 132 of the adjacent nanowell 136C.

For purposes herein, the first and second waveguides 520, 522 may function as a single array of waveguides. Each waveguide 520, 522 may be operable to illuminate well regions 132, 134 in a pair of adjacent nanowells 136. Additionally, it does not matter which well regions the waveguides illuminate in the pair of adjacent nanowells. For example, a waveguide 520 may illuminate two first well regions 132, two second well regions 134 or both a first and second well region 132, 134.

Figure 19:
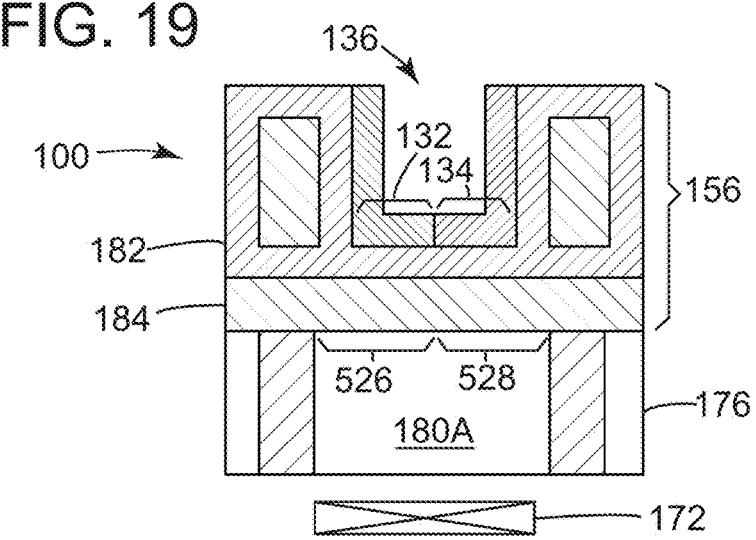
FIG. 19 depicts an example of a cross sectional view of an image sensor structure having first and second well regions disposed over first and second portions of a shared light guide, according to aspects described herein.

Referring to FIG. 19, an example is depicted of a cross sectional view of an image sensor structure 100 having first and second well regions 132, 134 disposed over first and second portions 526, 528 of a light guide 180A, according to aspects described herein. In this case, the forward strands 122 in the first well region 132 and reverse strands 124 in the second well region 134 may be excited simultaneously. Accordingly, the light detector 172 is shared by both first and second well regions 132, 134 and will receive both the brightest signal A (or bright cluster signal) and the second brightest signal B (or dim cluster signal) from those well regions at the same time. Assuming the intensity of each signal is approximately the same, then the chastity score for the combined signal will be approximately 50% and the contrast ratio will be about 1 to 1.

However, even with these low chastity scores and contrast ratios, there are signal processing techniques that may be used to determine the two types of bases that are fluorescing from the combined signal. Such techniques are detailed in U.S. Patent Application Publication 2019/0212295A1, titled: "SYSTEMS AND DEVICES FOR HIGH-THROUGHPUT SEQUENCING WITH SEMICONDUCTOR-BASED DETECTION", to Dehlinger et al., assigned to Illumina, Inc., and filed on Jan. 7, 2019, which is herein incorporated by reference in its entirety. One such technique is illustrated in FIGS. 20A, 20B and 21.

Figure 20A:
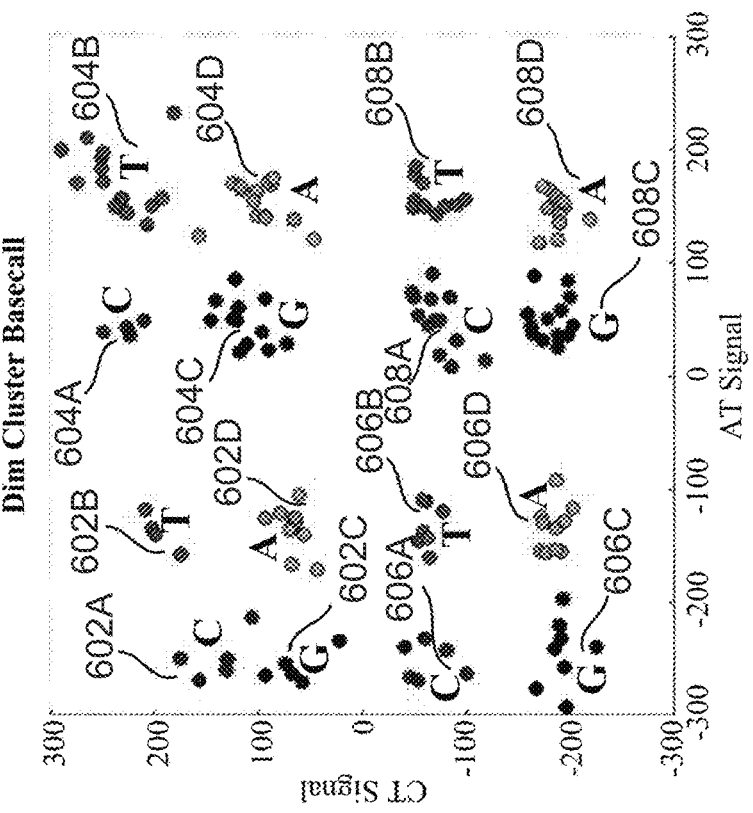
FIG. 20A depicts an example of a scatter plot of bright clusters, according to aspects described herein.
Figure 20B:
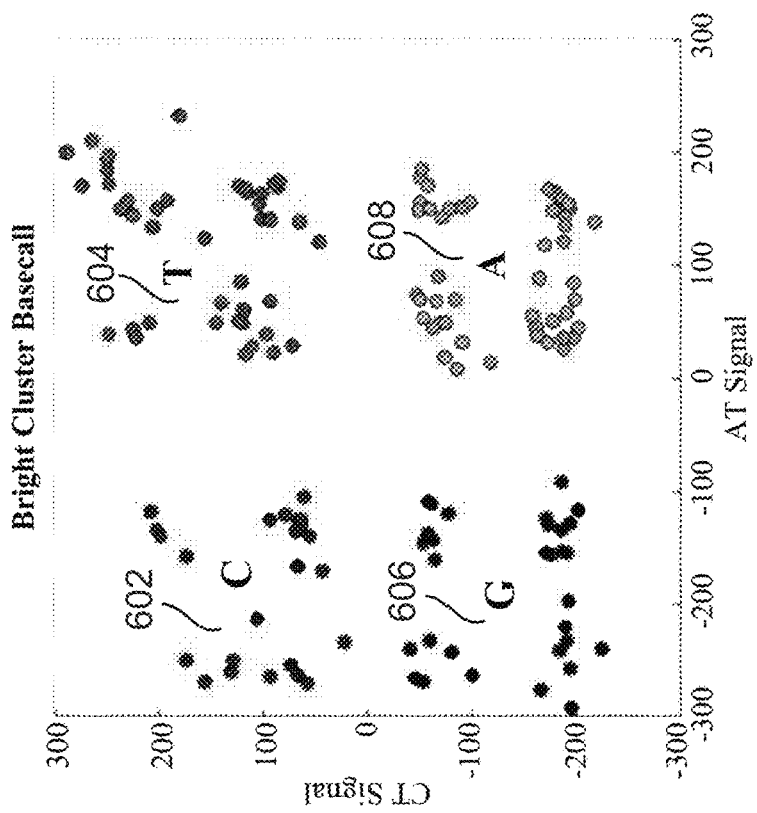
FIG. 20B depict an example of a scatter plot of dim clusters, according to aspects described herein.
Figure 21:
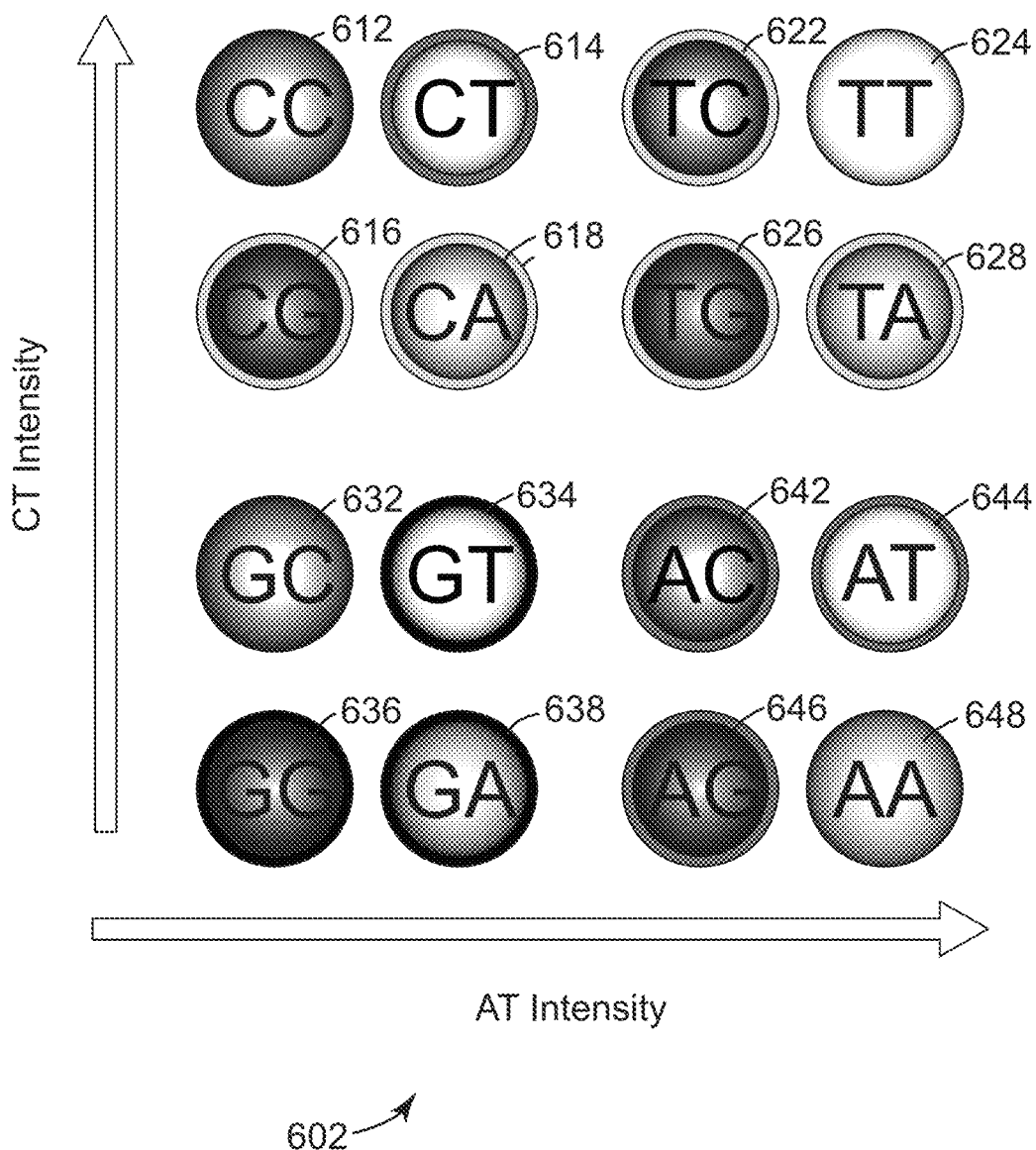
FIG. 21 depicts an example of a scatter plot that depicts 16 distributions produced by intensity values from bright and dim clusters, according to aspects described herein.

FIGS. 20A and 20B are scatter plots 600A and 600B that depict base calling of the bright and dim clusters using their respective pixel signals detected by the shared light detector 172 in accordance with one implementation. X-axis of the scatter plots 600A and 600B represents the AT pixel signals detected during a second illumination stage of the sampling event which induces illumination from a given cluster indicating nucleotide bases A and T. Y-axis of the scatter plots 600A and 600B represents the CT pixel signals detected during a first illumination stage of a sampling event which induces illumination from a given cluster indicating nucleotide bases C and T.

Scatter plot 600A shows four distributions 602, 604, 606, and 608 to which a signal processor (not show) classifies pixel signals from the bright cluster. In the illustrated implementation, distribution 602 represents nucleotide base C in the bright cluster, distribution 604 represents nucleotide base T in the bright cluster, distribution 606 represents nucleotide base G in the bright cluster, and distribution 608 represents nucleotide base A in the bright cluster.

Scatter plot 600B shows sixteen sub-distributions (or distributions) 602A-D, 604A-D, 606A-D, and 608A-D, with four sub-distributions for each of the four distributions 602, 604, 606, and 608 of the scatter plot 600A, to which the signal processor classifies pixel signals from the dim cluster. In the illustrated implementation, sub-distributions annotated with letter "A" represent nucleotide base C in the dim cluster, sub-distributions annotated with letter "B" represent nucleotide base T in the dim cluster, sub-distributions annotated with letter "C" represent nucleotide base G in the dim cluster, and sub-distributions annotated with letter "D" represent nucleotide base A in the dim cluster. In other implementations, different encodings of the bases may be used. When the signal processor classifies pixel signals from a dim cluster in one of the sixteen sub-distributions, the classification of the corresponding bright cluster is determined by the distribution which includes the dim cluster's sub-distribution. For example, if a dim cluster is classified to sub-distribution 608B (nucleotide base T), then the distribution for the corresponding bright cluster is 608 (nucleotide base A). As a result, the signal processor base calls the bright cluster as A and the dim cluster as T.

FIG. 21 is a scatter plot 602 that depicts sixteen distributions (or bins) produced by intensity values from bright and dim clusters of a cluster pair in accordance with one implementation. In implementations, the sixteen bins are produced over a plurality of base calling cycles. A signal processor combines pixel signals from the bright and dim clusters and maps them into one of the sixteen bins. When the combined pixel signals are mapped to bin 612 for a base calling cycle, the signal processor base calls the bright cluster as C and the dim cluster as C. When the combined pixel signals are mapped to bin 614 for the base calling cycle, the signal processor 138 base calls the bright cluster as C and the dim cluster as T. When the combined pixel signals are mapped to bin 616 for the base calling cycle, the signal processor 138 base calls the bright cluster as C and the dim cluster as G. When the combined pixel signals are mapped to bin 618 for the base calling cycle, the signal processor 138 base calls the bright cluster as C and the dim cluster as A.

Figure 22:
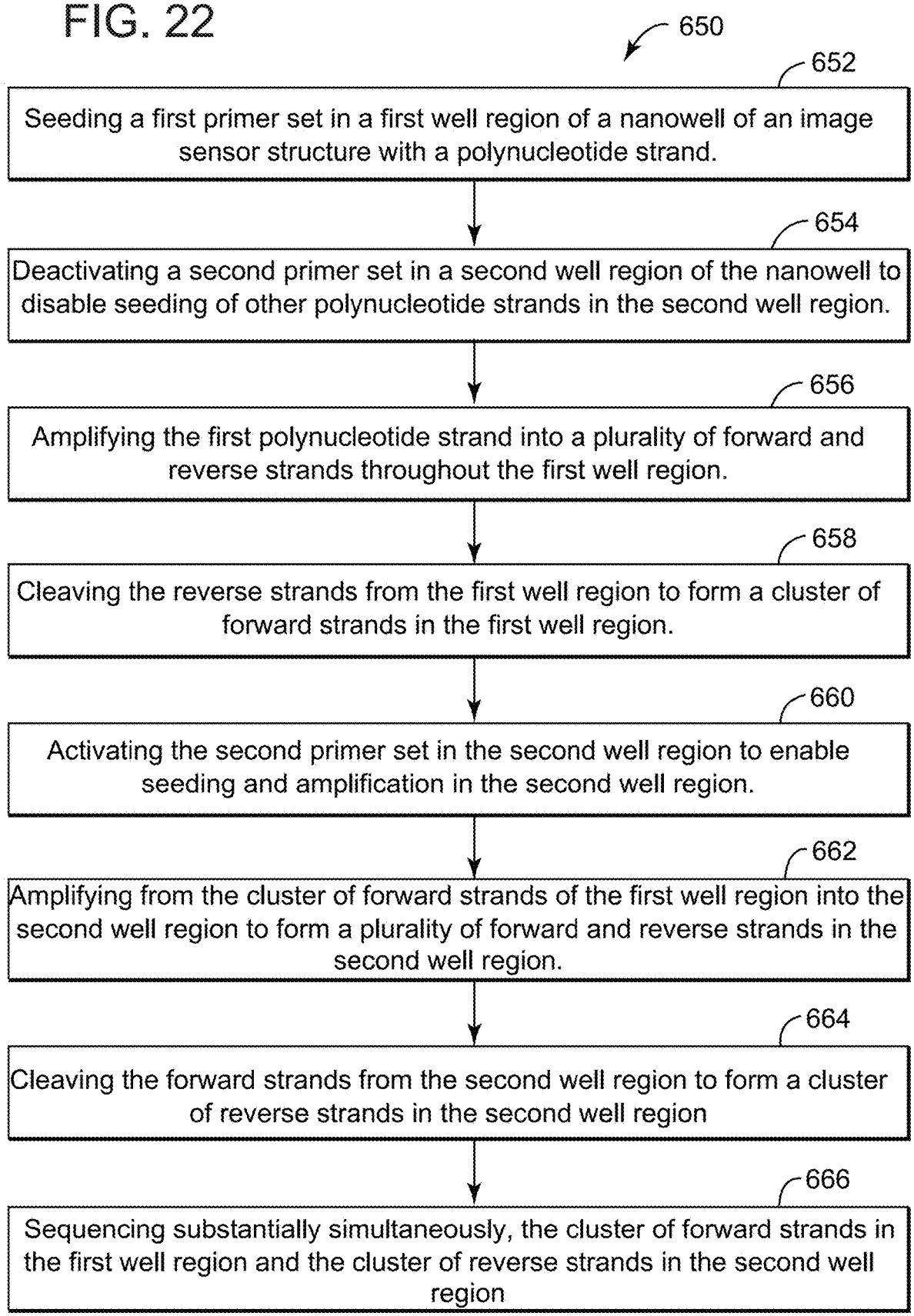
FIG. 22 depicts an example of a flow diagram of a method of simultaneous paired end sequencing, in accordance with aspects described herein.

Referring to FIG. 22, an example is depicted of a flow diagram of a method 650 of simultaneous paired end sequencing, in accordance with aspects described herein. The method may utilize one or more of the examples of image sensor structures 100 described herein.

This method 650 (FIG. 22), as well as the following methods 700 (FIG. 23), 750 (FIG. 24) and method 800 (FIG. 25), depict various steps of carrying out the methods. However, the order in which the steps of each method (650, 700, 750, 800) are executed may not coincide with the order in which the steps are illustrated in each of the FIGS. 22-25. For example, the following seeding step 652 may occur after the deactivating step 654.

The method at 652 includes seeding a first primer set 140 in a first well region 132 of a nanowell 136 of an image sensor structure 100 with a polynucleotide strand 110. The polynucleotide strand 110 (see FIG. 2) includes adapters 118 and 120 which attach to complementary primers 106, 108 (see FIG. 1) in the first well region 132 (see FIG. 7A).

At 654, a second primer set 142 in a second well region 134 of the nanowell 136 is deactivated to disable seeding of other polynucleotide strands in the second well region. The step may take place prior to the seeding step at 652. One example of deactivating the second well region 134 is to mask a protective layer over the second well region to prevent access of other polynucleotides to the second well region.

At 656 The first polynucleotide strand is amplified into a plurality of forward and reverse strands 106, 108 throughout the first well region 132. At 658, the reverse strands 108 are cleaved from the first well region 132 to form a forward strand cluster 121 in the first well region 132.

At 660, the second primer set 142 is then activated in the second well region 134 to enable seeding and amplification in the second well region 134. One example of activating the second well region 134 is to unmask any protective layer previously disposed over the second well region 134.

At 662 amplification then occurs from the forward strand cluster 121 of the first well region 132 into the second well region 134 to form a plurality of forward and reverse strands 106, 108 in the second well region 134. At 664, the forward strands 122 are cleaved from the second well region 134 to form a reverse strand cluster 123 in the second well region 134.

During the seeding (at 660) and amplification (at 662) processes in the second well region 134, no loose polynomial strands 110 are flowed into the flow channel 158 of the flow cell 112. Accordingly, no significant additional polyclonality due to loose polynomial strands 110 flowing into the second well region 134 through the flow channel 158 of the flow cell 112 may occur when seeding (at 660) and amplification (at 662) occurs in the second well region 134.

Once the forward and reverse strand clusters 121, 123 are formed in the first and second well regions 132, 134, simultaneous sequencing may occur at 666. In other words, at step 666, the forward strand cluster 121 in the first well region 132 and the reverse strand cluster 123 in the second well region 134 are sequenced substantially simultaneously.

Referring to FIG. 23, an example is depicted of a flow diagram of a method 700 of simultaneous paired end sequencing, in accordance with aspects described herein. Method 700 is a subset of method 650, in that it is an expansion of the simultaneous sequencing step 666.

At 702, the method 700 includes attaching first complementary nucleotides 126 (see FIG. 5) having first fluorescent tags 128 to nucleotides 116 of the forward strand cluster 121 in the first well region 132. At 704, second complementary nucleotides 126 having second fluorescent tags 128 are attached to nucleotides 116 of the reverse strand cluster 123 in the second well region 134.

At 706, the method radiates excitation light 186 substantially simultaneously onto the forward strand cluster 121 and the reverse strand cluster 123 (see FIG. 7A) to fluoresce emissive light 174 from the first and second tags 128. At 708, the emissive light 174 is transmitted substantially simultaneously from the first and second tags 128. The emissive light 174 from the first tags 128 transmits through a first light guide 180A (see FIG. 7A) to a first light detector 172. The emissive light 174 from the second tags 128 transmits through a second light guide 180B to a second light detector 174 to determine the sequence of nucleotides of the forward and reverse strands 122, 124 respectively.

In order to reduce polyclonality while executing the methods 650 or 700, the first well region 132 may have an area that is smaller than an area of the second well-region 134. For example, the area of the first well region 132 may be no more than 90%, no more than 80% or no more than 70% or the area of the second well region 134.

In order to reduce both polyclonality and crosstalk between the first and second light guides 180A, 180B, the first and second well regions 132, 134 may have a combined shape that looks generally like a dog bone (see FIG. 10). More specifically, the first well region 132 may include a first section 196 and a second section 198. The first section 196 of well region 132 may be disposed over the entire first light guide 180A, wherein the first section 196 has a first section width 201. The first section 196 may have an area that is only slightly larger than the area of the light guide 180A in order to reduce polyclonality. For example, the area of the first section 196 may be no more than 5%, no more than 10% or no more than 15% larger than the area of the top surface of the light guide 180A.

The second section 198 of well region 134 may extend from the first section 196 to a region interface 138 between the first and second well regions 132, 134. The second section 198 may have a second section width 194 that is less than the first section width 201.

Additionally, the second well region 134 may include a third section 202 and a fourth section 204. The third section 202 of the second well region 134 may be disposed over the entire second light guide 180B and have a third section width 206. The fourth section 204 may extend from the third section 202 to the region interface 138. The fourth section 204 may have a fourth section width 194 that is less than the third section width 206. Also, the width 194 of the fourth section 204 may be substantially equal to the width 194 of the second section 198.

By reducing the widths 194 of the second and fourth sections 198, 204, the interface region 138 is reduced. Reducing the interface region 138 substantially reduces the chance of any polyclonality in the first well region 132 from amplifying over into the second well region 134. Additionally, reducing the interface region 138 also substantially reduces the chance of any crosstalk occurring between the first and second well regions 132, 134.

Another way to reduce crosstalk while executing the methods 650 or 700, is to dispose an opaque layer 400 between the first and second light guides 180A, 180B and the first and second well regions 132, 134. The opaque layer 400 (see FIG. 12) may extend under the entire region interface 138 of the first and second well regions 132, 134. The opaque layer 400 may cover less than an entire portion of the first and second light guides (see FIGS. 13A-13C).

Referring to FIG. 24, an example is depicted of a flow diagram of a method 750 of simultaneous paired end sequencing, in accordance with aspects described herein. Method 750 is a subset of method 650, in that it is an expansion of the simultaneous sequencing step 666.

At 752, the method 750 includes attaching first complementary nucleotides 126 (see FIG. 5) having first fluorescent tags 128 to nucleotides 116 of the forward strand cluster 121 in the first well region 132. At 754, second complementary nucleotides 126 having second fluorescent tags 128 are attached to nucleotides 116 of the reverse strand cluster 123 in the second well region 134.

At 756, a substantially larger amount of excitation light 186 is radiated onto the forward strand cluster 121 than onto the reverse strand cluster 123 to fluoresce a substantially larger amount of emissive light 174 from the first tags 128 than from the second tags 128. At 758, the emissive light 174 from the first tags 128 is transmitted through a first light guide 180A to a first light detector 172 to determine the nucleotides of the forward strands 122. At 760, a substantially larger amount of excitation light 186 is radiated onto the reverse strand cluster 123 than onto the forward strand cluster 121 to fluoresce a substantially larger amount of emissive light 174 from the second tags 128 than from the first tags 128. At 762, the emissive light 174 from the second tags 128 is transmitted through the first light guide 180A to the first light detector 172 to determine the nucleotides of the reverse strands 124.

The method 750 may, for example, be executed with an image sensor structure 100 similar to that illustrated in FIG. 16, wherein a first well region 132 is disposed over a first portion 526 of a first light guide 180A and a second well region 134 is disposed over a second portion 528 of the first light guide 180A. A waveguide layer 524 is disposed between the first light guide 180A and the first and second well regions 132, 134. A first waveguide 520 is disposed in the waveguide layer 524, wherein the first waveguide 520 extends under the first well-region 132, but not under the second well region 134. A second waveguide 522 is disposed in the waveguide layer 524, wherein the second waveguide 522 extends under the second well-region 134, but not under the first well region 132.

Alternatively, the method 750 may, for example, be executed with an image sensor structure 100 similar to that illustrated in FIG. 17, wherein each nanowell 136 of an array of nanowells 136 includes a first well region 132 disposed over a first portion 526 of a first light guide 180A and a second well region 134 disposed over a second portion 528 of the first light guide 180A. A passivation stack 156 is disposed over a device stack 176 of the image sensor structure 100, wherein the array of nanowells 136 is disposed in the passivation stack 156. Each first waveguide 520 of an array of first waveguides 520 is disposed in the passivation stack 156 adjacent a side 530 of the first waveguide's associated nanowell 136. Each second waveguide 522 of an array of second waveguides 522 is disposed in the passivation stack 156 adjacent an opposing side 532 of the second waveguide's associated nanowell 136.

Utilizing the above structure, excitation light 186 may be radiated through the first waveguide 520 and primarily onto the forward strand cluster 121. Then emissive light 174, primarily from the forward strand cluster 121, may be transmitted through the first light guide 180A to the light detector 172 for analysis. Thereafter, excitation light 186 may be radiated through the second waveguide 522 and primarily onto the reverse strand cluster 123. Then emissive light 174, primarily from the reverse strand cluster 123, may be transmitted through the first light guide 180A to the light detector 172 for analysis.

Referring to FIG. 25, an example is depicted of a flow diagram of a method 800 of simultaneous paired end sequencing, in accordance with aspects described herein. Method 800 is a subset of method 650, in that it is an expansion of the simultaneous sequencing step 666.

At 802, the method 800 includes attaching first complementary nucleotides 126 (see FIG. 5) having first fluorescent tags 128 to nucleotides 116 of the forward strand cluster 121 in the first well region 132. At 804, second complementary nucleotides 126 having second fluorescent tags 128 are attached to nucleotides 116 of the reverse strand cluster 123 in the second well region 134.

At 806, excitation light 186 is radiated substantially simultaneously onto the forward strand cluster 121 in the first well region 132 and onto the reverse strand cluster 123 in the second well region 134 to fluoresce emissive light 174 from the first and second tags 128. At 808, the combined emissive light 174 from the first and second well regions 132, 134 is transmitted from the first and second tags 128 through a first light guide 18A to a first light detector 172. Signal processing techniques may then be utilized to determine nucleotides in the forward and reverse strands 122, 124 associated with the combined emissive light 174 detected in the first light detector 172. Examples of such signal processing techniques are discussed herein with reference to FIGS. 20A, 20B and 21. The method 800 may, for example, be executed with an image sensor structure 100 similar to that illustrated in FIG. 19.

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

Although the invention has been described by reference to specific examples, it should be understood that numerous changes may be made within the spirit and scope of the inventive concepts described. Accordingly, it is intended that the disclosure not be limited to the described examples, but that it have the full scope defined by the language of the following claims.

What is claimed is:

1. An image sensor structure, comprising:
   an image layer comprising an array of light detectors disposed therein;
   a device stack disposed over the image layer;
   an array of light guides disposed in the device stack, each light guide associated with a light detector of the array of light detectors;
   an array of nanowells disposed over the device stack, each nanowell of the array of nanowells associated with a first light guide of the array of light guides, each first light guide associated with a first light detector of the array of light detectors;
   a first primer set disposed throughout a first well region of each nanowell; and
   a different second primer set disposed throughout a second well region of each nanowell, the second well region adjacent the first well region at a region interface;
   wherein the first and second primer sets are operable to attach a forward strand cluster of forward polynucleotide strands in the first well region and to attach an adjacent reverse strand cluster of reverse polynucleotide strands in the second well region.

2. The image sensor structure of claim 1, comprising:
   each nanowell of the array of nanowells associated with a second light guide of the array of light guides, each second light guide associated with a second light detector of the array of light detectors;
   the first well region disposed over the first light guide; and
   the second well region disposed over the second light guide.

3. The image sensor structure of claim 2, wherein an area of the first well region is smaller than an area of the second well region.

4. The image sensor structure of claim 2, comprising:
   the first well region comprising:
      a first section that is disposed over the entire first light guide, the first section having a first section width, and
      a second section extending from the first section to the region interface, the second section having a second section width that is less than the first section width; and
   the second well region comprising:
      a third section that is disposed over the entire second light guide, the third section having a third section width, and
      a fourth section extending from the third section to the region interface, the fourth section having a fourth section width that is less than the third section width,
   wherein the second section width of the first well region and the fourth section width of the second well region are substantially equal.

5. The image sensor structure of claim 4, comprising:
   the first section and third sections having substantially circular shapes;
   wherein the first and third section widths are diameters of the first and third sections respectively.

6. The image sensor structure of claim 2, comprising:
   an opaque layer disposed between the array of light guides and the first and second well regions of each nanowell;
   the opaque layer extending under the entire region interface of the first and second well regions; and
   the opaque layer covering less than an entire portion of top surfaces the first and second light guides associated with each nanowell.

7. The image sensor structure of claim 2, comprising:
   the first light guide associated with a first light detector of the array of light detectors;
   the second light guide associated with a second light detector of the array of light detectors;
   each nanowell associated with the first and second light guides having a width that is less than the pitch between the first and second light detectors; and
   the first and second light guides extending from their associated nanowell to their associated first and second light detectors at an acute angle relative to each other.

8. The image sensor structure of claim 1, comprising:
   the first well region of each nanowell disposed over a first portion of the associated first light guide;
   the second well region of each nanowell disposed over a second portion of the associated first light guide;
   an array of first waveguides disposed over the device stack, each first waveguide associated with a nanowell of the array of nanowells, each first waveguide operable to illuminate excitation light on a forward strand cluster of forward polynucleotide strands attached in the first well-region of the first waveguide's associated nanowell; and an array of second waveguides disposed over the device stack, each second waveguide associated with a nanowell of the array of nanowells, each second waveguide operable to illuminate excitation light on a reverse strand cluster of reverse polynucleotide strands attached in the second well-region of the second waveguide's associated nanowell.

9. The image sensor structure of claim 8, comprising:
a waveguide layer disposed between the array of light guides and the first and second well regions of each nanowell;
each first waveguide of the array of waveguides disposed in the waveguide layer and extending under the first well region of the first waveguide's associated nanowell; and
each second waveguide of the array of waveguides disposed in the waveguide layer and extending under the second well region of the second waveguide's associated nanowell.

10. The image sensor structure of claim 8, comprising:
a passivation stack disposed over the device stack, where the array of nanowells is disposed in the passivation stack;
each first waveguide of the array of first waveguides disposed in the passivation stack adjacent a side of the first waveguide's associated nanowell; and
each second waveguide of the array of waveguides disposed in the passivation stack adjacent an opposing side of the second waveguide's associated nanowell.

11. The image sensor structure of claim 10, wherein:
each first waveguide of the array of first waveguides is operable to illuminate excitation light on a cluster of polynucleotide strands attached in the first or second well-region of a nanowell adjacent to the first waveguide's associated nanowell; and
each second waveguide of the array of second waveguides is operable to illuminate excitation light on a cluster of polynucleotide strands attached in the first or second well-region of a nanowell adjacent to the second waveguide's associated nanowell.

12. A method comprising:
seeding a first primer set in a first well region of a nanowell of an image sensor structure with a polynucleotide strand;
deactivating a second primer set in a second well region of the nanowell to disable seeding of other polynucleotide strands in the second well region;
amplifying the first polynucleotide strand into a plurality of forward and reverse strands throughout the first well region;
cleaving the reverse strands from the first well region to form a forward strand cluster in the first well region;
activating the second primer set in the second well region to enable seeding and amplification in the second well region;
amplifying from the forward strand cluster of the first well region into the second well region to form a plurality of forward and reverse strands in the second well region;
cleaving the forward strands from the second well region to form a reverse strand cluster in the second well region; and sequencing substantially simultaneously the forward strand cluster in the first well region and the reverse strand cluster in the second well region.

13. The method of claim 12, wherein sequencing substantially simultaneously comprises:
attaching first complementary nucleotides having first fluorescent tags to nucleotides of the forward strand cluster in the first well region,
attaching second complementary nucleotides having second fluorescent tags to nucleotides of the reverse strand cluster in the second well region,
radiating excitation light substantially simultaneously onto the forward strand cluster and the reverse strand cluster to fluoresce emissive light from the first and second tags,
receiving substantially simultaneously the emissive light from the first tags through a first light guide to a first light detector and the emissive light from the second tags through a second light guide to a second light detector to determine the sequence of nucleotides of the forward and reverse strands respectively.

14. The method of claim 13, wherein:
the first well region comprises:
a first section that is disposed over the entire first light guide, the first section having a first section width, and
a second section extending from the first section to a region interface between the first and second well regions, the second section having a second section width that is less than the first section width; and
the second well region comprises:
a third section that is disposed over the entire second light guide, the third section having a third section width, and
a fourth section extending from the third section to the region interface, the fourth section having a fourth section width that is less than the third section width.

15. The method of claim 13, wherein an opaque layer is disposed between the first and second light guides and the first and second well regions, the opaque layer extends under an entire region interface of the first and second well regions and the opaque layer covers less than an entire portion of the first and second light guides.

16. The method of claim 13, wherein:
the nanowell has a width that is less than a pitch between the first and second light detectors; and
the first and second light guides extend to their associated first and second light detectors at an acute angle relative to each other.

17. The method of claim 12, wherein:
the first well-region is disposed over a first portion of a first light guide; and
the second well-region is disposed over a second portion of the first light guide.

18. The method of claim 12, wherein sequencing substantially simultaneously comprises:
attaching first complementary nucleotides having first fluorescent tags to nucleotides of the forward strand cluster;
attaching second complementary nucleotides having second fluorescent tags to nucleotides of the reverse strand cluster;
radiating a substantially larger amount of excitation light onto the forward strand cluster than onto the reverse strand cluster to fluoresce a substantially larger amount of emissive light from the first tags than from the second tags;

receiving the emissive light from the first tags through a first light guide to a first light detector to determine the nucleotides of the forward strands;

radiating a substantially larger amount of excitation light onto the reverse strand cluster than onto the forward strand cluster to fluoresce a substantially larger amount of emissive light from the second tags than from the first tags; and receiving the emissive light from the second tags through the first light guide to the first light detector to determine the nucleotides of the reverse strands.

19. The method of claim 18, wherein:

a first waveguide is disposed over the first light guide;

a second waveguide is disposed over the first light guide;

the excitation light is radiated through the first waveguide and onto the forward strand cluster; and the excitation light is radiated through the second waveguide and onto the reverse strand cluster.

20. The method of claim 12, wherein sequencing substantially simultaneously comprises:

attaching first complementary nucleotides having first fluorescent tags to nucleotides of the forward strand cluster, attaching second complementary nucleotides having second fluorescent tags to nucleotides of the reverse strand cluster, radiating excitation light substantially simultaneously onto the forward strand cluster in the first well region and onto the reverse strand cluster in the second well region to fluoresce emissive light from the first and second tags, receiving combined emissive light from the first and second tags through a first light guide to a first light detector; and utilizing signal processing techniques to determine nucleotides in the forward and reverse strands associated with the combined emissive light detected in the first light detector.

* * * * *